(12) United States Patent
Gavish et al.

(10) Patent No.: US 10,035,780 B2
(45) Date of Patent: Jul. 31, 2018

(54) QUINAZOLINE SCAFFOLD BASED COMPOUNDS, PHARMACEUTICAL COMPOSITIONS AND METHODS OF USE THEREOF

(71) Applicant: TECHNION RESEARCH & DEVELOPMENT FOUNDATION LTD., Haifa (IL)

(72) Inventors: Moshe Gavish, Tel-Aviv (IL); Jehuda Arieh Veenman, Naharia (IL); Alex Shterenberg, Petah Tikva (IL); Ilan Marek, Haifa (IL); Alex Vainshtein, Haifa (IL); Avraham Avital, Sarid (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 0 days.

(21) Appl. No.: 15/304,958

(22) PCT Filed: Apr. 22, 2015

(86) PCT No.: PCT/IL2015/050426
§ 371 (c)(1),
(2) Date: Oct. 18, 2016

(87) PCT Pub. No.: WO2015/162615
PCT Pub. Date: Oct. 29, 2015

(65) Prior Publication Data
US 2017/0217907 A1    Aug. 3, 2017

Related U.S. Application Data

(60) Provisional application No. 61/982,880, filed on Apr. 23, 2014.

(51) Int. Cl.
C07D 239/91    (2006.01)
(52) U.S. Cl.
CPC .................................. C07D 239/91 (2013.01)
(58) Field of Classification Search
CPC .................................................. C07D 239/90
See application file for complete search history.

(56) References Cited

U.S. PATENT DOCUMENTS

| 4,499,094 A | 2/1985 | Dubroeucq et al. |
| 4,684,652 A | 8/1987 | Dubroeucq et al. |
| 6,765,006 B2 | 7/2004 | Upasani et al. |
| 8,541,428 B2 * | 9/2013 | Gavish ............... C07D 239/90 514/266.1 |
| 2004/0248890 A1 | 12/2004 | Gonzalez, III et al. |

FOREIGN PATENT DOCUMENTS

| JP | 2004256473 | 9/2004 |
| WO | 9640646 | 12/1996 |
| WO | 9740020 | 10/1997 |
| WO | 2008023357 A1 | 2/2008 |
| WO | 2015162615 | 10/2015 |

OTHER PUBLICATIONS

Vippagunta et al. (2001).*
Wolff et al. (1976).*
M.E. Wolff, Burger's Medicinal Chemistry and Drug Discovery, 5th Ed. vol. I (1995).*
Banker et al., "Modern Pharmaceuticals", pp. 596 3rd Ed. (1996).*
International Search Report PCT/IL2015/050426 Completed Jul. 20, 2016; dated Jul. 28, 2016 6 Pages.
Written Opinion PCT/IL2015/050426 Completed Jul. 20, 2016 8 Pages.
Abdel-Megeed MF and Abderrahman Teniou A (1988) Synthesis of some 3-substituted 4(3H)-quinazolinone and 4(3H)-quinazolinethione derivatives and related fused biheterocyclic ring systems. Collect Czech Chem Commun 53: 329-335.
Ammar et al., (1989) Synthesis and effect of gamma irradiation on some new 6,8-dichloro-4-(3H)-quinazolinones of biological interest. Current Science 58(22): 1231-1234.
Anwar M (1981) The absorption spectra of some 4 (3H)-quinazolinones. Pakistan Journal of Scientific and Industrial Research 24(1): 8-13. XP002692312.
Azarashvili et al., (2007) The peripheral-type benzodiazepine receptor is involved in control of Ca 2+-induced permeability transition pore opening in rat brain mitochondria. Cell calcium, 42(1), 27-39.
Benavides et al., (1983) Labelling of "peripheral-type" benzodiazepine binding sites in the rat brain by using [3H]PK 11195, an isoquinoline carboxamide derivative: kinetic studies and autoradiographic localization. J Neurochem 41(6): 1744-50.
Berge et al., (1977) Pharmaceutical salts. J Pharm Sci 66(1): 1-19.
Betlazar et al., (2016) The impact of high and low dose ionising radiation on the central nervous system. Redox biology, 9, 144-156.
Bode et al., (2014) Modulation of gene expression associated with the cell cycle and tumorigenicity of glioblastoma cells by the 18 kDa Translocator Protein (TSPO). Austin J Pharmacol Ther, 2(10), 1053.

(Continued)

*Primary Examiner* — Paul V Ward
(74) *Attorney, Agent, or Firm* — The Roy Gross Law Firm, LLC; Roy Gross

(57) ABSTRACT

The present invention relates to novel heterocyclic compounds based on a quinazoline scaffold, which bind effectively to the mitochondrial translocator protein (TSPO), and counteract cell death processes. These compounds can also stimulate neuronal differentiation. The present invention further relates to pharmaceutical compositions including such compounds, and methods of using these compounds for the prevention and treatment of brain damage resulting from brain injury, especially secondary brain damage due to traumatic brain injury (TBI). The compounds of the invention are also useful in preventing, treating, and curing brain damage due to neurodegenerative diseases, including underlying and associated pathological and mental disorders. The compounds can also be used to prevent and treat brain damage due to infection, toxic challenges, and excessive drug use, e.g., recreational, over the counter, or prescription drugs. These compounds can also prevent heart failure, for example associated with brain injuries and brain diseases.

17 Claims, 16 Drawing Sheets

(56) References Cited

OTHER PUBLICATIONS

Bourguignon (1996) Identical and nonidentical twin drugs. In "Practice of Medicinal Chemistry", edited by C.G. Wermuth, Academic Press, London, 1996, pp. 261-293.
Bradford, (1976) A rapid and sensitive method for the quantitation of microgram quantities of protein utilizing the principle of protein-dye binding. Analytical biochemistry, 72(1-2), 248-254.
Buchwald et al., (1980) Long-term, continuous intravenous heparin administration by an implantable infusion pump in ambulatory patients with recurrent venous thrombosis. Surgery 88(4): 507-16.
Byrnes et al., (2009) Metabotropic glutamate receptors as targets for multipotential treatment of neurological disorders. Neurotherapeutics, 6(1), 94-107.
Caballero et al., (2014) Concentration-dependent bimodal effect of specific 18 kDa translocator protein (TSPO) ligands on cell death processes induced by ammonium chloride: Potential implications for neuropathological effects due to hyperammonemia. CNS & Neurological Disorders—Drug Targets (Formerly Current Drug Targets—CNS & Neurological Disorders), 13(4), 574-592.
Cagnin et al., (2006) In vivo evidence for microglial activation in neurodegenerative dementia. Acta Neurologica Scandinavica, 114(s185), 107-114.
Camins et al., (2008) Apoptotic mechanisms involved in neurodegenerative diseases: experimental and therapeutic approaches. Methods and findings in experimental and clinical pharmacology, 30(1), 43-65.
Campiani et al., (1996) Synthesis, biological activity, and SARs of pyrrolobenzoxazepine derivatives, a new class of specific "peripheral-type" benzodiazepine receptor ligands. J Med Chem 39(18): 3435-50.
Chelli et al., (2004) Peripheral benzodiazepine receptor ligands: mitochondrial transmembrane potential depolarization and apoptosis induction in rat C6 glioma cells. Biochemical pharmacology, 68(1), 125-134.
Coronado et al., (2011) Surveillance for traumatic brain injury-related deaths—United States, 1997-2007. Morbidity and mortality weekly report. Surveillance summaries (Washington, DC: 2002), 60(5), 1-32.
Dadon-Nachum et al., (2011) Stem cells treatment for sciatic nerve injury. Expert opinion on biological therapy, 11(12), 1591-1597.
Danovich et al., (2008) The influence of clozapine treatment and other antipsychotics on the 18 kDa translocator protein, formerly named the peripheral-type benzodiazepine receptor, and steroid production. European Neuropsychopharmacology, 18(1), 24-33.
Database Caplus, chemical abstracts service, Columbus, Ohio, US; 1961, DD19629: XP002692306, Database accession No. 1961: 118616. Compounds 110330-75-1.
Database Caplus, chemical abstracts service, Columbus, Ohio, US; Sep. 16, 2004 (Sep. 16, 2004), JP2004256473: XP002692307, retrieved from STN Database accession No. 2004: 753404. Compounds 757968-04-0 & JP 2004256473 A (Ono Pharmaceutical Co) Sep. 16, 2004 (Sep. 16, 2004).
Database registry [online] Chemical abstracts service, Columbus, Ohio, US;2004, retrieved from STN Database accession No. 684234-45-5.
Database registry [online] Chemical abstracts service, Columbus, Ohio, US; 2002, retrieved from STN Database accession No. 397300-59-3.
Database registry [online] Chemical abstracts service, Columbus, Ohio, US; 2002, retrieved from STN Database accession No. 392734-64-4.
Database registry [online] Chemical abstracts service, Columbus, Ohio, US; 2001, retrieved from STN Database accession No. 374908-45-9.
Database registry [online] Chemical abstracts service, Columbus, Ohio, US; 2001, retrieved from STN Database accession No. 374772-28-8.
Database registry [online] Chemical abstracts service, Columbus, Ohio, US; 2001, retrieved from STN Database accession No. 364615-21-4.
Database registry [online] Chemical abstracts service, Columbus, Ohio, US;2001, retrieved from STN Database accession No. 364610-67-3.
Database registry [online] Chemical abstracts service, Columbus, Ohio, US; 2001, retrieved from STN Database accession No. 333742-07-7.
Deniau et al., (2003) A New Synthetic Route to Highly Enantioenriched 3-Substituted 2,3-Dihydro-1 H-isoindol-1-ones. Tetrahedron: Asym 14: 2253-2258.
Desai and Desai (2005) Heterocyclic synthesis: A convenient route to some 2-mercepto 1,3,4-oxadiazole and green chemistry microwave-induced one-pot synthesis of 2-aryl 1,3,4-oxadiazole in quinazolone and their antibacterial and antifungal activity. J Heterocyclic Chem 42(5): 995-999.
El-Khawaga et al., (1981) Synthesis of peptides containing a quinazolin-4-one moiety. Gazzetta Chimica Italiana 111(9-10): 441-442. XP009166956.
Finnie, (2001) Animal models of traumatic brain injury: a review. Australian veterinary journal, 79(9), 628-633.
Gaetz, (2004) The neurophysiology of brain injury. Clinical Neurophysiology, 115(1), 4-18.
Gaitner Michal, M.Sc. thesis, 2004 (abstract).
Galiegue et al., (2003) The peripheral benzodiazepine receptor: a promising therapeutic drug target. Curr Med Chem 10(16): 1563-72.
Gavish et al, (1999) Enigma of the peripheral benzodiazepine receptor. Pharmacological reviews, 51(4), 629-650.
Ghajar, (2000) Traumatic brain injury. The Lancet, 356(9233), 923-929.
Giza et al., (2013) Summary of evidence-based guideline update: Evaluation and management of concussion in sports Report of the Guideline Development Subcommittee of the American Academy of Neurology. Neurology, 80(24), 2250-2257.
Gupta et al., (1982) Amoebicidal and fungicidal activities of new quinazolones. Arzneimittelforschung 32(6): 598-600. XP009166959.
Gut et al., (2013) Whole-organism screening for gluconeogenesis identifies activators of fasting metabolism. Nature chemical biology, 9(2), 97-104.
Hanefeld et al., (1996) 3-(2,5-Dioxopyrrolidin-1-yl), 3-(2,6-dioxopiperidin-1-yl), and 3-(1,3-10 dioxoisoindolin-2-yl) rhodanines. A novel type of rhodanine derivatives J Heterocyclic Chem 33: 1443-1146.
Hatty & Banati, (2015) Protein-ligand and membrane-ligand interactions in pharmacology: the case of the translocator protein (TSPO). Pharmacological research, 100, 58-63.
Kassab (2005) Synthesis and behavior of 4-(4'-chloro-3'methylphenyl)-1(2H)-phthalazinone towards certain electrophiles and nucleophiles. Egyp J Chem 48(2): 183-199.
Khalifa et al., (1995) Synthesis of some quinazolone derivatives with tuberculostatic activity. Zagazig Journal of Pharmaceutical Sciences 4(1-B): 287-293.
Khalin et al., (2016) A mouse model of weight-drop closed head injury: emphasis on cognitive and neurological deficiency. Neural regeneration research, 11(4), 630.
King Jr et al., (2005) Early Glasgow Outcome Scale scores predict long-term functional outcome in patients with severe traumatic brain injury. Journal of neurotrauma, 22(9), 947-954.
Kluger et al., (2004) The special injury pattern in terrorist bombings. Journal of the American College of Surgeons, 199(6), 875-879.
Kugler et al., (2005) Abstracts of the 14th Annual Meeting of the Israel Society for Neuroscience, and the Joint Germany-Israel Meeting, Eilat, Israel 16: S38.
Kugler et al., (2008) Ligands of the mitochondrial 18 kDa translocator protein attenuate apoptosis of human glioblastoma cells exposed to erucylphosphohomocholine. Analytical Cellular Pathology, 30(5), 435-450.
Kuznetsov et al., (2005) Abstract Viewer/Itinerary Planner. Washington, DC: Society for Neuroscience, Online: 2005; Program No. 673.4.
Langer and Arbilla (1988) Imidazopyridines as a tool for the characterization of benzodiazepine receptors: a proposal for a

(56) References Cited

OTHER PUBLICATIONS pharmacological classification as omega receptor subtypes. Pharmacol Biochem Behav 29(4): 763-6.
Lemoine et al., (1990) Footshock affects heart and brain MAO and MAO inhibitory activity and open field behavior in rats. Pharmacology Biochemistry and Behavior, 36(1), 85-88.
Levin et al., (2005) The peripheral-type benzodiazepine receptor and tumorigenicity: isoquinoline binding protein (IBP) antisense knockdown in the C6 glioma cell line. Biochemistry, 44(29), 9924-9935.
Li et al., (2016) Translocator protein 18 kDa (TSPO): an old protein with new functions?. Biochemistry, 55(20), 2821-2831.
Liu et al., (2017) Functional gains in energy and cell metabolism after TSPO gene insertion. Cell Cycle, 16(5), 436-447.
Ma et al., (2016) TSPO ligand PK11195 alleviates neuroinflammation and beta-amyloid generation induced by systemic LPS administration. Brain research bulletin, 121, 192-200.
Maaser et al., (2001) Specific ligands of the peripheral benzodiazepine receptor induce apoptosis and cell cycle arrest in human colorectal cancer cells. Br J Cancer 85(11): 1771-80.
Mammen et al., (1998) Polyvalent interactions in biological systems: Implications for design and use of multivalent ligands and inhibitors Angew Chem Int Ed 37(20): 2755.
Marshall, (2000) Head Injury: Recent Past, Present, and Future. Neurosurgery, 47(3), 546-561.
Mattson & Kraemer, (2003) Mitochondria in cell death: novel targets for neuroprotection and cardioprotection. Trends in molecular medicine, 9(5), 196-205.
McEnery et al., (1992) Isolation of the mitochondrial benzodiazepine receptor: association with the voltage-dependent anion channel and the adenine nucleotide carrier. Proceedings of the National Academy of Sciences, 89(8), 3170-3174.
Misra et al., (1978) Synthesis of quinazolone substituted amides and piperazonium salts of quinazolone substituted acids as possible anticonulsants. Journal of the Indian Chemical Society LV: 1046-1048 XP002692308.
Nakamura & Lipton, (2010) Redox regulation of mitochondrial fission, protein misfolding, synaptic damage, and neuronal cell death: potential implications for Alzheimer's and Parkinson's diseases. Apoptosis, 15(11), 1354-1363.
Panickar et al., (2007) Downregulation of the 18-kDa translocator protein: Effects on the ammonia-induced mitochondrial permeability transition and cell swelling in cultured astrocytes. Glia, 55(16), 1720-1727.
Panikashvill et al., (2001) An endogenous cannabinoid (2-AG) is neuroprotective after brain injury. Nature, 413(6855), 527.
Papadopoulos & Lecanu, (2009) Translocator protein (18 kDa) TSPO: an emerging therapeutic target in neurotrauma. Experimental neurology, 219(1), 53-57.
Papadopoulos et al., (2006) Translocator protein (18kDa): new nomenclature for the peripheral-type benzodiazepine receptor based on its structure and molecular function. Trends in pharmacological sciences, 27(8), 402-409.
Quatman-Yates et al., (2016) Physical rehabilitation interventions for post-mTBI symptoms lasting greater than 2 weeks: systematic review. Physical therapy, 96(11), 1753-1763.
Reddy (2000) Synthesis and spectral studies of iron(III) and iron(II) complexes with 2,3-disubstituted quinazolin-4(3H)-ones. Indian Journal of Chemistry Section A: Inorganic, Bio-inorganic, Physical, Theoretical & Analytical Chemistry 39A(11): 1202-1206.
Rosenberg et al., (2014) In vitro effect of FGIN-1-27, a ligand to 18 kDa mitochondrial translocator protein, in human osteoblast-like cells. Journal of bioenergetics and biomembranes, 46(3), 197.
Rossi & Volterra, (2009) Astrocytic dysfunction: insights on the role in neurodegeneration. Brain research bulletin, 80(4), 224-232.
Rupprecht et al., (2010) Translocator protein (18 kDa)(TSPO) as a therapeutic target for neurological and psychiatric disorders. Nature reviews Drug discovery, 9(12), 971-988.

Ryu et al., (2005) Peripheral benzodiazepine receptor ligand PK11195 reduces microglial activation and neuronal death in quinolinic acid-injected rat striatum. Neurobiol Dis 20(2): 550-61.
Saito et al., (2001) A new and convenient synthesis of 3-aryl-3-hydroxyisoindol-1-ones and their aza analogs. Synthesis 2: 221.
Saudek et al., (1989) A preliminary trial of the programmable implantable medication system for insulin delivery. N Engl J Med 321(9): 574-9.
Scholz et al., (2015) Targeting translocator protein (18 kDa)(TSPO) dampens pro-inflammatory microglia reactivity in the retina and protects from degeneration. Journal of neuroinflammation, 12(1), 201.
Shargorodsky et al., (2012) The nitric oxide donor sodium nitroprusside requires the 18 kDa Translocator Protein to induce cell death. Apoptosis, 17(7), 647-665.
Shternberg Alexander, M.Sc. thesis, 2006 (abstract).
Soustiel et al., (2008) Neuroprotective effect of Ro5-4864 following brain injury. Experimental neurology, 214(2), 201-208.
Soustiel et al., (2008) The effect of oxygenation level on cerebral post-traumatic apoptotsis is modulated by the 18-kDa translocator protein (also known as peripheral-type benzodiazepine receptor) in a rat model of cortical contusion. Neuropathology and applied neurobiology, 34(4), 412-423.
Sullivan et al., (2005) Mitochondrial permeability transition in CNS trauma: cause or effect of neuronal cell death?. Journal of neuroscience research, 79(1-2), 231-239.
Sullivan et al., (2005) Mitochondrial permeability transition in CNS trauma: cause or effect of neuronal cell death? J Neurosci Res 79(1-2): 231-9.
Vainshtein et al., (2015) Quinazoline-based tricyclic compounds that regulate programmed cell death, induce neuronal differentiation, and are curative in animal models for excitotoxicity and hereditary brain disease. Cell death discovery, 1, 15027.
Van Muijlwijk-Koezen et al., (2000) Isoquinoline and quinazoline urea analogues as antagonists for the human adenosine A(3) receptor. J Med Chem 43(11): 2227-2238.
Veenman & Gavish, (2000) Peripheral-type benzodiazepine receptors: their implication in brain disease. Drug development research, 50(3-4), 355-370.
Veenman & Gavish, (2006) The peripheral-type benzodiazepine receptor and the cardiovascular system. Implications for drug development. Pharmacology & therapeutics, 110(3), 503-524.
Veenman & Gavish, (2012) The role of 18 kDa mitochondrial translocator protein (TSPO) in programmed cell death, and effects of steroids on TSPO expression. Current molecular medicine, 12(4), 398-412.
Veenman et al., (2002) PK 11195 attenuates kainic acid-induced seizures and alterations in peripheral-type benzodiazepine receptor (PBR) protein components in the rat brain. Journal of neurochemistry, 80(5), 917-927.
Veenman et al., (2004) Peripheral-type benzodiazepine receptor density and in vitro tumorigenicity of glioma cell lines. Biochemical pharmacology, 68(4), 689-698.
Veenman et al., (2007) Channel-like functions of the 18-kDa translocator protein (TSPO): regulation of apoptosis and steroidogenesis as part of the host-defense response. Current pharmaceutical design, 13(23), 2385-2405.
Veenman et al., (2008) VDAC activation by the 18 kDa translocator protein (TSPO), implications for apoptosis. Journal of bioenergetics and biomembranes, 40(3), 199-205.
Veenman et al., (2012) Effects of 18-kDa translocator protein knockdown on gene expression of glutamate receptors, transporters, and metabolism, and on cell viability affected by glutamate. Pharmacogenetics and genomics, 22(8), 606-619.
Veenman et al., (2014) Apoptosis induction by erucylphosphohomocholine via the 18 kDa mitochondrial translocator protein: implications for cancer treatment. Anti-Cancer Agents in Medicinal Chemistry (Formerly Current Medicinal Chemistry-Anti-Cancer Agents), 14(4), 559-577.
Veenman et al., (2015) TSPO as a target for treatments of diseases, including neuropathological disorders. Cell death & disease, 6(10), e1911.

(56) References Cited

OTHER PUBLICATIONS

Veenman et al., (2016) Tetrapyrroles as endogenous TSPO ligands in eukaryotes and prokaryotes: comparisons with synthetic ligands. International journal of molecular sciences, 17(6), 880.

Veiga et al., (2005) Ro5-4864, a peripheral benzodiazepine receptor ligand, reduces reactive gliosis and protects hippocampal hilar neurons from kainic acid excitotoxicity. Journal of neuroscience research, 80(1), 129-137.

Veiga et al., (2007) Translocator protein (18 kDa) is involved in the regulation of reactive gliosis. Glia, 55(14), 1426-1436.

Vippagunta et al., (2001) Crystalline solids. Adv Drug Deliv Rev 48(1): 3-26.

Wang et al., (2016) Global deletion of TSPO does not affect the viability and gene expression profile. PloS one, 11(12), e0167307.

Weisinger et al., (2004) Peripheral benzodiazepine receptor antisense knockout increases tumorigenicity of MA-10 Leydig cells in vivo and in vitro. Biochemistry, 43(38), 12315-12321.

Wu et al., (2015) Rasagiline and selegiline suppress calcium efflux from mitochondria by PK11195-induced opening of mitochondrial permeability transition pore: a novel anti-apoptotic function for neuroprotection. Journal of Neural Transmission, 122(10), 1399-1407.

Yanni et al., (1987) Synthesis of some new sulfonamides containing a quinazolinone moiety of biological interest. Bulletin of the Faculty of Science 16(1): 55-59. XP002692313.

Yasin et al., (2017) Classical and Novel TSPO Ligands for the Mitochondrial TSPO Can Modulate Nuclear Gene Expression: Implications for Mitochondrial Retrograde Signaling. International journal of molecular sciences, 18(4), 786.

Zeno et al., (2009) CoCl2 induces apoptosis via the 18 kDa translocator protein in U118MG human glioblastoma cells. Biochemistry, 48(21), 4652-4661.

International Search Report of PCT/IL2015/050426 Completed Jul. 20, 2015; dated Jul. 28, 2015 4 pages.

Written Opinion of PCT/IL2015/050426 Completed Jul. 20, 2015; dated Jul. 28, 2015 8 pages.

\* cited by examiner

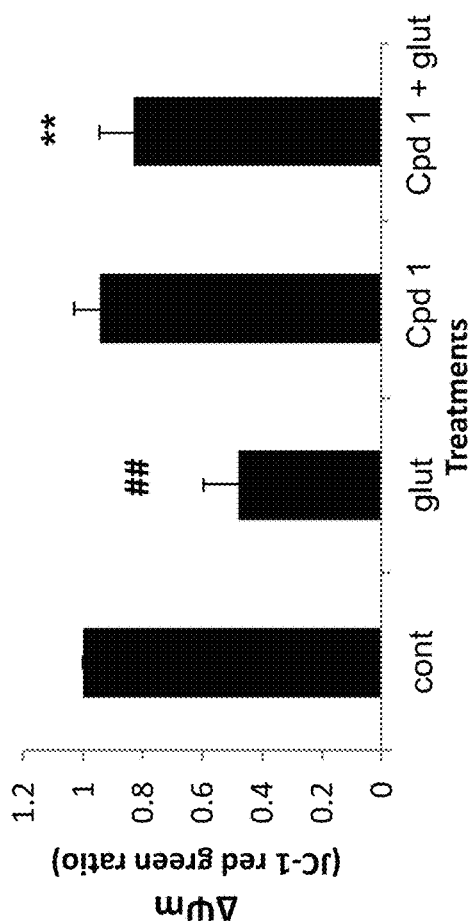
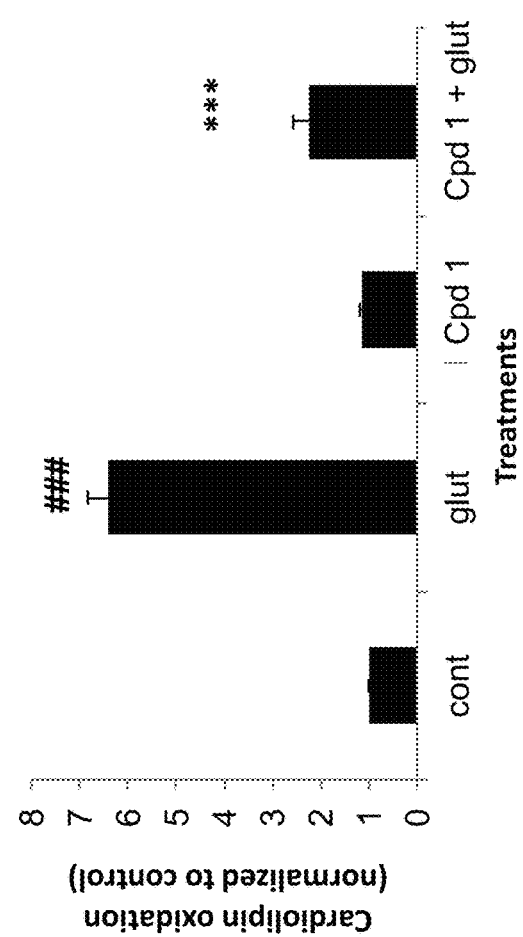
Figure 1B
Figure 1C
Figure 1

Differentiation of PC12 cells due to application of Cpd 1

QUINAZOLINE SCAFFOLD BASED COMPOUNDS, PHARMACEUTICAL COMPOSITIONS AND METHODS OF USE THEREOF

RELATED APPLICATIONS

This application is a national stage application under 371 of PCT/IL2015/050426 filed on Apr. 22, 2015, and claims the benefit of U.S. provisional patent application Ser. No. 61/982,880 filed on Apr. 23, 2014. The disclosure of both applications are incorporated herein by reference in their entirety.

FIELD OF THE INVENTION

The present invention relates to heterocyclic compounds based on a quinazoline scaffold which bind effectively to the mitochondrial translocator protein (TSPO), and counteract cell death processes. The present invention further provides pharmaceutical compositions including such compounds, and methods of using these compounds, especially for treating and preventing neurodegenerative diseases as well as brain damage due to acute events (e.g., traumatic brain injury (TBI) or its after effects), or chronic challenges (e.g., infection, toxins, or drug use), including the underlying pathological processes.

BACKGROUND OF THE INVENTION

Neurodegeneration due to neurodegenerative brain disease and injury is a major health and economic concern. Current models predict at least a more than threefold rise in the total number of persons with Alzheimer's disease between 2000 and 2050. A well accepted concept for a basic cause for neurodegeneration is overexcitation by glutamate as well as impairments of mitochondria leading to death of nerve cells in the brain (Camins et al. *Methods Find Exp Clin Pharmacol.* 2008; 30:43-65; Nakamura et al. *Apoptosis.* 2010; 15:1354-63). Potential treatments have been designed and tested, for example, by inhibition of glutamate receptors. However, such approaches have not matured to effective treatments, probably because the causes for neurodegeneration are not well understood (Byrnes et al. *Neurotherapeutics.* 2009; 6:94-107). Alternative approaches have therefore been explored, for example by preventing mitochondria-based cell death processes (Veenman et al. *Drug Dev Res.* 2000; 50:355-370; Veenman et al. *Neurochem.* 2002; 80:917-27; Mattson et al. *Trends Mol Med.* 2003; 9:196-205). Furthermore, glia constitutes the vast majority of brain cells, and serves to maintain and protect healthy neurons. Indeed it is now well realized that glia presents a critical factor in the progress of neurodegeneration (Rossi et al. *Brain Res Bull.* 2009; 80:224-32). Thus, glia should be one of the factors to be included for the development of effective treatments for neurodegeneration.

Traumatic brain injury (TBI) is characterized by sudden physical damage to the brain. It is caused by many factors including warfare, terrorism, motor vehicle accidents and other traffic accidents, work related accidents, sports injuries, violent crimes, household accidents, child abuse and domestic violence, or by an object passing through the skull, for example gunshot wounds, etc. The physical, behavioral, and/or mental changes that may result from TBI depend on the areas of the brain that are injured. Injuries include focal and diffuse brain damage. Focal damage is confined to a small area of the brain. The focal damage is most often at the point where the head hits an object or where an object, such as a bullet, enters the brain. Diffuse damage is spread throughout the brain. While treatment of head wounds immediately after injury has improved steadily in the past few decades, lingering effects such as disabilities are still likely after moderate and severe TBI (Kluger et al. *J Am Coll Surg.* 2004; 199:875-79). It is now well understood that the primary injury of TBI is followed for hours and days by a process of secondary brain injury (Gaetz et al. *Clin Neurophysiol.* 2004; 115:4-18; Sullivan et al. *J Neurosci Res.* 2005; 79:231-39). Major factors contributing to this second wave of brain damage include: excitatory amino acids such as glutamate, $Ca^{++}$ homeostasis, and reactive oxygen species (ROS) (Kluger et al. 2004, Gaetz et al. 2004). Mitochondria are one of the cell organelles affected by secondary brain injury and in particular collapse of the mitochondrial membrane potential ($\Delta\Psi m$) appears to take a central role among the factors leading to neuronal cell death due to secondary brain injury and neurodegenerative diseases (Kluger et al. 2004; Gaetz et al. 2004). This suggests that targeting the regulation of the $\Delta\Psi m$, immediately after sustained brain injury, would have significant therapeutic implications for TBI. As the TSPO is a major component for these mechanisms, targeting the TSPO to treat secondary brain injury, neurodegenerative diseases, and related conditions represents a novel and potentially very effective therapeutic approach.

Importantly, the TSPO has been associated with the voltage dependent anion channel (VDAC), located in the outer mitochondrial membrane, which functions as a major channel allowing passage of small molecules and ions between the mitochondrial inter-membrane space and cytoplasm (McEnery et al. *Proc Natl Acad Sci USA.* 1992; 89:3170-4; Veenman et al. *Anticancer Agents Med Chem.* 2014; 14:559-77). Opening of the VDAC can contribute to collapse of the $\Delta\Psi m$. The TSPO has also been associated the adenine nucleotide translocator (ANT), which is located in the inner mitochondrial membrane, and can form a lethal pore also contributing to collapse of the $\Delta\Psi m$. The discovery of TSPO's essential role in programmed cell death processes, including collapse of the $\Delta\Psi m$, related to neurodegeneration, as it can occur due to disease and brain trauma, has exemplified the TSPO as a target for drug development for neurodegenerative diseases and treatment of brain trauma. In this context, TSPO was found to be involved in the generation of ROS that take part in the induction of the mitochondrial apoptosis cascade, as well as other forms of programmed cell death. These ROS are known to cause detachment of cytochrome c from cardiolipins located at the inner mitochondrial membrane. In addition, ROS contribute to pore opening in the outer mitochondrial membrane allowing release of cytochrome c into the cytosol. This forms the initiating step for activation of the mitochondrial apoptosis pathway (Veenman et al. *J Bioenerg Biomembr.* 2008; 40:199-205; Veenman et al. 2014). These data provide an understanding regarding the mechanisms whereby TSPO may serve as a target to modulate programmed cell death rates. This has implications for drug design to treat diseases such as neurodegeneration and the effects of brain trauma, and other forms of brain damage, in particular involving cell death in the brain.

TSPO was first detected by its capability to bind benzodiazepines in peripheral tissues and later was detected also in glial cells in the brain, hence its previous name peripheral benzodiazepine receptor (PBR) (Papadopoulos et al. *Trends Pharmacol Sci.* 2006; 27:402-9; Veenman and Gavish. *Pharmacol Ther.* 2006; 110:503-24; Veenman et al. *Curr*

*Pharm Design.* 2007; 13:2385-2405). It is known that this mitochondrial protein can be pharmacologically regulated by specific ligands (Veenman et al. *J Neurochem.* 2002; 80:917-27; Veenman and Gavish. *Pharmacol Ther.* 2006; 110:503-24; Veenman et al. 2007). Typical examples of classical TSPO ligands are PK 11195 and Ro5 4864 (PK 11195 is an isoquinoline derivative and Ro5 4864 is a benzodiazepine). TSPO functions include: regulation of cell death processes, regulation of the cell cycle, regulation of gene expression, modulation of steroid production, involvement in cell migration, involvement in cell differentiation, involvement in angiogenesis, involvement in excitotoxic cell death, and involvement in inflammation and immune responses. The expression of TSPO is enhanced during neurodegeneration occurring, e.g., in Alzheimer, Parkinson, and Huntington disease, and also due to brain trauma (Gavish et al. *Pharmacol Rev.* 1999; 51:629-50; Veenman and Gavish. 2000; 50:355-70; Veenman and Gavish. 2006; Veenman and Gavish. *Curr Mol Med.* 2012; 12:398-412; Veenman et al. *Pharmacogenet Genomics.* 2012; 22:606-19; Veiga et al. *Glia.* 2007; 55:1426-36; Papadopoulos et al. *Exp Neurol.* 2009; 219:53-7). In the CNS, the primary cellular location of TSPO is astrocytes and microglia. However, TSPO can also be expressed in neurons that are on a cell death pathway. Silencing the TSPO by genetic manipulation (siRNA and antisense RNA) prevents programmed cell death, including cell death induced by glutamate. Interestingly, TSPO levels are increased in U118MG cells exposed to lethal levels of glutamate. U118MG cells are of astrocytic origin. For at least these reasons, the TSPO presents a promising target to protect the brain from neuropathological processes (Veiga et al. 2007; Panickar et al. *Glia.* 2007; 55:1720-7). Apart from its role in cell death, other elucidated functions under the control of the TSPO, such as regulation of gene expression, involvement in inflammation and immune response, involvement in cell migration, cell differentiation, involvement in angiogenesis, and its specific involvement in excitotoxic cell death, emphasize the importance of the TSPO as a target for treatment against cell death in the brain due to disease and brain trauma, including its contribution to repair and restorative mechanisms (Bode et al. *Pharmacogenet Genomics.* 2012; 22:538-50; Veenman et al. *Pharmacogenet Genomics.* 2012). It has previously been found that the classical TSPO ligands PK 11195 and Ro5 4864 present moderate neuroprotective effects in vivo (see, e.g., Veenman et al. 2002; Veiga et al. 2005; 80:129-37; Veenman Gavish. 2012). The effects of classical TSPO ligands in vitro approximate those found by silencing TSPO by genetic manipulation (Veenman et al. *Biochem Pharmacol.* 2004; 68:689-98; Kugler et al. *Cell Oncol.* 2008; 30:435-50; Veenman et al. 2008; Levin et al. *Biochemistry.* 2005; 44:9924-35; Zeno et al. *Biochemistry.* 2009; 48:4652-61).

U.S. Pat. No. 8,541,428 discloses phthalazine, quinazoline, and quinoxaline derivatives, pharmaceutical compositions containing the compounds, and their therapeutic use in treating and preventing brain damage resulting from traumatic brain injuries (TBI), and in treating and preventing neurodegenerative diseases. Compounds disclosed in said patent publication were shown to bind to the PBR (TSPO) with varying affinity and were shown to reduce cell death induced by glutamate in cell culture. Furthermore, cell protection conferred by these compounds occurred with neuronal type cells (SH SY 5Y) as well as glial cell types (U118MG).

U.S. Pat. No. 6,765,006 discloses quinazolines and other heterocycles which are antagonists or positive modulators of AMPA receptors, and the use thereof for treating, preventing or ameliorating neuronal loss or treating or ameliorating neurodegenerative diseases.

A need in the art exists to develop improved agents that bind effectively to the TSPO, combined with the effect of preventing brain cell death, including various forms of programmed cell death (apoptosis, necrosis, autophagic cell death), as it occurs due to TBI and secondary brain damage and/or neurodegenerative diseases. Furthermore, for successful treatment of TBI, secondary brain damage, and neurodegenerative disease it is further desired that repair mechanisms are activated and/or facilitated.

SUMMARY OF THE INVENTION

The present invention relates to compounds described by formula (I), as well as individual compounds described herein, which are based on a quinazoline scaffold substituted with an amide group and an attached rotatable phenyl group optionally substituted by a halogen. The present invention further relates to pharmaceutical compositions containing the compounds, and their therapeutic use in treating and preventing brain injuries resulting from acute or chronic events and their after effects, as well as treatment of brain damage associated with brain diseases that include degeneration of neurons and/or glial cells. The compounds of the invention also inhibit mechanisms of programmed cell death (i.e., they prevent cell death), and they can stimulate cell activity related to replenishing of dead brain cells. The compounds of the invention bind effectively to the 18 kDa mitochondrial Translocator Protein (TSPO) and inhibit its cell death function. Thus, these compounds have specific cell death preventing properties and thereby neuroprotective properties, both for neurons themselves as well as the glial cells maintaining neuron health. By attenuating cell death processes induced by glutamate, which is known to be an important agent causing secondary brain damage after traumatic brain damages, and also one of the toxic agents during neurodegeneration, the compounds of the present invention prevent cell death in the brain. These compounds also protect against other agents that are part of secondary brain damage and neurodegeneration as well as other pathological conditions (for example, but not restricted to, glutamate, glutamate receptor ligands other than glutamate, hypoxia mimicking agents, beta-amyloids, nitric oxide generating agents, apoptosis inducing agents, steroids, ammonium chloride, toxic compounds, interference with ATP production, etc.). These compounds also activate differentiation of cells, making them useful to stimulate restorative processes in diseased and damaged CNS. As such, the compounds of the invention are useful in treating and preventing diseases and conditions, including neurodegenerative diseases and brain injuries, associated with programmed cell death pathways. The compounds of the invention are further useful in treating or preventing cardiovascular dysfunction, such as those associated with Huntington Disease.

In general, the compounds of the invention may be used in one or more of the following modes of action: 1) prophylactically; 2) counteracting progressing damage (e.g., brain damage) and disease (e.g., neurodegeneration); 3) stimulating self-repair; and 4) supporting replacement of diseased and damage tissue by grafts/transplants. The broad applicability of the compounds presented herein is due to their ability to modulate processes common to the disease and progressing damage associated therewith (such as cell death) as well as their ability to differentiate specific cell types to the desired form of mature cells.

In one embodiment, the present invention provides a compound represented by the structure of formula (I):

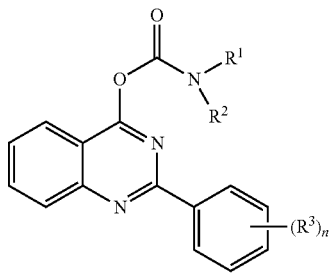

wherein
R¹ and R² are each independently a linear or branched $C_1$-$C_{12}$ alkyl;
R³ is a halogen; and
n is 0, 1, 2, 3, 4 or 5;
with the proviso that, when n is 0, R¹ is different from R²;
including salts, solvates, polymorphs, and mixtures thereof.

In one embodiment, R¹ and R² are each a $C_1$-$C_4$ alkyl, preferably R¹ and R² are different from each other. In some embodiments, one of R¹ and R² is methyl, and the other is ethyl.

In another embodiment, the compound is represented by the structure of formula (I), wherein R¹ and R² are the same (thereby forming a symmetric amide), and n is other than 0 (i.e. the compound has one or more halogen substituents on the phenyl ring). In another currently preferred embodiment, the compound is represented by the structure of formula (I), wherein R¹ and R² are different from each other (thereby forming an asymmetric amide). According to the principles of the present invention, when n is 0 (i.e., R³ does not exist), R¹ and R² are different from each other. However, for halogenated derivatives in which n is other than 0, then R¹ and R² may be the same (symmetric amides) or different from each other (asymmetric amides). Each possibility represents a separate embodiment of the present invention.

In one particularly preferred embodiment, the compound is represented by the structure of formula (I), wherein n is other than 0 and R¹ and R² are different from each other, thereby forming an asymmetric amide, having a halogenated phenyl substituent.

In some embodiments, the present invention teaches how to systematically improve the desired characteristics of therapeutically active compounds, including but not restricted to protection against cell death induced by glutamate in cell culture, by specific, targeted modifications in the structures of the compounds of the invention (i.e. modifications of the alkyl side chains and halogenations, Cl for example, of the rotatable phenyl ring).

Representative compounds of the invention are selected from compounds 1, 2, 3, 4, 5, 6, 7 and 8, with compound 1, compound 5 and compound 6 being currently preferred. The structures of compounds 1 to 8 are provided in the detailed description hereinbelow.

In one embodiment, the present invention provides a pharmaceutical composition comprising a pharmaceutically acceptable carrier, and as an active ingredient a compound represented by formula (I) or a compound of any of formulae 1, 2, 3, 4, 5, 6, 7 or 8.

In certain embodiments, the described pharmaceutical composition is in a form suitable for oral, parenteral, transdermal, topical, or rectal administration, administration by inhalation, administration via a suppository or administration via dialysis. Each possibility represents a separate embodiment of the present invention.

The compounds of the invention are unexpectedly more potent than the compounds disclosed in U.S. Pat. No. 8,541,428, as well as classical TSPO ligands, as they combine effective TSPO binding with good protection against cell death, as for example demonstrated herein in cell culture. In animal studies, as for example demonstrated herein, compound 1 of the present invention enhances lifespan and improves locomotor activity of transgenic R6-2 mice, an animal model for the neurodegenerative motor disease of Huntington, while Compound A, the most potent compound described in U.S. Pat. No. 8,541,428, as well as the classical TSPO ligand, PK 11195, had no such effects in this animal model. Halogenation of the compounds appears to be very effective as demonstrated by robust lifespan enhancing and tremor reducing effects of compound 5 and compound 6 in the R6-2 transgenic mouse model for the human neurodegenerative disease of Huntington disease.

In one embodiment, it has been unexpectedly discovered that increasing the chain length of the amide moiety of compounds of formula (I) substantially increases the binding affinity to the TSPO. For example, compound 7 of the present invention (R¹, R²=ethyl) binds with substantially higher affinity to the TSPO (Ki≈2.5 nm), as compared with compound A (R¹, R²=methyl, Ki≈600 nm). This discovery was completely unexpected, and represents one embodiment of the present invention.

In another embodiment, it has unexpectedly been discovered that a compound comprising an asymmetric amide is more potent than its counterparts having symmetric amides. Without wishing to be bound by any particular mechanism or theory, it is contemplated that the asymmetry is important both for the combination of affinity to TSPO and the capability to prevent cell death, as well as counteracting neurodegenerative processes in both animals and man. None of the compounds described in U.S. Pat. No. 8,541,428 have an asymmetric amide moiety. The discovery of the combined effect of the asymmetric amides, which contributes both to the affinity of the compounds to TSPO as well as their ability to prevent cell death, and to ameliorate neurodegenerative processes, could not have been foreseen. In particular, based on comparisons between compounds of U.S. Pat. No. 8,541,428 among themselves, as demonstrated herein, and with classical TSPO ligands, e.g., PK 11195 and Ro5 4864, it has been discovered that enhanced TSPO affinity is sometimes associated with loss of protective capacities. As contemplated herein, the applicants have now unexpectedly discovered that novel compounds of formula (I) have both effective affinity for the TSPO combined with cell protective properties in cell culture, and protective effects regarding the neurodegenerative disease of Huntington in an animal model. These findings were completely unexpected and constitute one embodiment of the present invention.

It has further unexpectedly been discovered that several quinazoline derivatives, having halogen-substituents on the phenyl ring efficiently protect well against cell death. Furthermore, it has been discovered that some configurations of halogen substituents on the phenyl ring modulate binding to TSPO, providing potent compounds that bind the TSPO and protect against cell death. Thus, in some embodiments, halogen substituent(s) on the phenyl ring, alone or in combination with the nature of the alkyl substituents on the amide side chain, substantially affect the combination of binding properties and cell protective functions of the novel compounds described by formula (I). U.S. Pat. No. 8,541,428 does not exemplify any halogenated derivatives nor any asymmetric amides at all. Therefore, quinazoline derivatives of formula (I), which comprise at least one halogen moiety on the phenyl ring, and/or an asymmetric amide present, constitute additional embodiments of the present invention. Based on the discovery of the effect of the asymmetric alkyl moieties of the amide group, it is now contemplated that halogens located on the rotatable phenyl ring in interaction with these moieties, can affect binding to the TSPO as well as control of TSPO function, including its regulation of cell death.

As contemplated herein, it has also been discovered that incorporation of halogen(s) on the rotatable phenyl ring does not necessarily significantly affect binding to TSPO, however, the presence of halogens prevents or reduces undesired lethal effects in cell culture induced by high concentrations (100 μM) of compound of the same structure but lacking the halogenation. Furthermore, the protective effects of halogenated compounds against glutamate-induced cell death are better than or equal to those of the corresponding non-halogenated analogs. As such, halogenated compounds present a particular advantage in that they can be more protective and are less toxic and may be associated with a reduced side effect profile as compared with non-halogenated derivatives.

Another advantage of the compounds of the present invention, for example compound 1, is that they are stable over several months of storage, with little batch to batch variation in properties. In addition to the ability to target TSPO's capability of cell death control to prevent TBI and neurodegenerative processes, it was furthermore found with microarray studies that TSPO knockdown led to major changes in gene expression of glutamate receptors, transporters, and enzymes in human astrocyte type cells (Veenman et al., 2012b). Thus, short term treatment with the compounds of the present invention may prevent cell death by blocking collapse of the mitochondrial membrane potential ($\Delta\Psi$m), while long term treatment, as for example achieved by stable knockdown of TSPO expression, or by chronic inhibition with TSPO ligands, can regulate gene expression to counteract neurodegenerative processes. Furthermore, because of TSPO's capability to regulate the cell cycle, development, migration, differentiation, and adhesion of cells, via TSPO's effects on gene expression (Bode et al. 2012; Veenman et al. 2012), targeting the TSPO may stimulate differentiation of stem cells lining the ventricular wall and their migration to diseased brain areas where they can replace damaged neurons. Thus, the present invention includes the capability of the compounds described herein to affect mitochondrial regulated cell processes, as well as gene expression in relation to brain damage in the aftermath of brain trauma, as well as in relation to neurodegenerative diseases (Bode et al. 2012; Veenman et al. 2012). Indeed, it was discovered that the new compounds described herein, in combination with glutamate, can stimulate PC12 cells in culture to differentiate to neuron like cells. This combination of protective and repair processes affected by regulation of the TSPO by the novel compounds described herein, presents a new unique feature of the present invention.

The compounds or pharmaceutical compositions described above are useful for a variety of modes of treatment. In some embodiments, the compound or pharmaceutical composition is given as prophylactic treatment to subjects in high risk groups including: subjects engaging in high risk activities, an infant or child at risk for developing a neurodevelopmental disorder associated with brain damage and/or neurodegeneration, a subject at risk for having a hereditary disease associated with brain damage and/or neurodegeneration, and/or a subject at risk for developing age related neurological diseases associated with brain damage and/or neurodegeneration. In other embodiments, the compound or pharmaceutical composition is given during injury or disease progression as a counteracting treatment. In certain embodiments, the compound or pharmaceutical composition is given as, or in addition to, counteracting treatment in order to stimulate self-repair processes in the brain. In some other embodiments, the compound or pharmaceutical composition is given as treatment to support transplants of cells and tissue repair in a subject in need thereof. Each possibility represents a separate embodiment of the present invention.

Thus, in some embodiments, the present invention provides a method for treating or preventing brain damage and/or progression and/or symptoms thereof, by administering to a subject in need thereof an effective amount of a compound or a pharmaceutical composition as described above. In one embodiment, the brain damage is due to brain injury resulting from an acute event such as traumatic brain injury (TBI). In another embodiment, the brain damage is due to a secondary brain damage resulting from TBI. In yet another embodiment, the brain damage is a secondary brain damage resulting from agents that are involved in secondary brain damage or neurodegeneration, for example glutamate, glutamate receptor ligands other than glutamate, hypoxia mimicking agents, nitric oxide generating agents, apoptosis inducing agents, steroids, ammonium chloride, toxic compounds, and agents which interfere with ATP production. In other embodiments, the brain damage is due to an acute or chronic challenge resulted from an infection, exposure to toxins, and excessive drug use of recreational, over the counter, and/or prescription drugs. Each possibility represents a separate embodiment of the present invention.

In another aspect, the present invention further provides a method for preventing, reducing or treating CNS damage by activating migration, proliferation, adhesion, and/or differentiation, to thereby replenish depleted brain cells in a subject having brain damage due to injury, or who is at risk for developing brain damage due to injury, by administering to the subject an effective amount of a compound or a pharmaceutical composition as described above.

The present invention further provides a method of treating or preventing a neurodegenerative disease or a symptom thereof, comprising the step of administering to a subject in need thereof an effective amount of a compound or a pharmaceutical composition as described above.

In one particular aspect, the present invention provides a method for preventing neurodegeneration by preventing programmed cell death in a subject having a neurodegenerative disease or who is at risk for developing a neurodegenerative disease, comprising the step of administering to the subject an effective amount of a compound or a pharmaceutical composition as described above.

In other embodiments, the present invention provides a method for preventing, reducing or treating CNS damage by activating migration, proliferation, adhesion, and/or differentiation, to thereby replenish depleted brain cells in a subject having a neurodegenerative disease or who is at risk for developing a neurodegenerative disease, comprising the step of administering to the subject an effective amount of a compound or a pharmaceutical composition as described above.

In certain embodiments, the neurodegenerative disease is selected from the group consisting of Alzheimer's Disease, Parkinson's Disease, Huntington disease, Lou Gehrig Disease, Multiple Sclerosis, autoimmune disorders, Pick Disease, diffuse Lewy body disease, progressive supranuclear palsy (Steel-Richardson syndrome), multisystem degeneration (Shy-Drager syndrome), motor neuron diseases, amyotrophic lateral sclerosis, degenerative ataxias, cortical basal degeneration, ALS-Parkinson's-Dementia complex of Guam, subacute sclerosing panencephalitis, synucleinopathies, primary progressive aphasia, striatonigral degeneration, Machado-Joseph Disease/spinocerebellar ataxia type 3 and olivopontocerebellar degenerations, Gilles De La Tourette disease, bulbar and pseudobulbar palsy, spinal and spinobulbar muscular atrophy (Kennedy Disease), primary lateral sclerosis, familial spastic paraplegia, Werdnig-Hoffmann Disease, Kugelberg-Welander Disease, Tay-Sach Disease, Sandhoff Disease, familial spastic disease, Wohlfart-Kugelberg-Welander Disease, spastic paraparesis, progressive multifocal leukoencephalopathy, prion diseases, Creutzfeldt-Jakob Disease, Gerstmann-Straussler-Scheinker Disease, Kuru, and fatal familial insomnia. Each possibility represents a separate embodiment of the present invention.

In another aspect, the present invention further provides a method of stimulating or enhancing restorative processes in the CNS, including migration of progenitor cells to damaged brain areas, neurodifferentiation in damaged brain areas, and re-establishment of damaged neurocircuitry, comprising the step of administering to a subject in need thereof an effective amount of a compound or a pharmaceutical composition as described above.

In another aspect, the present invention provides a method for preventing, reducing or treating brain edema, comprising the step of administering to a subject in need thereof an effective amount of a compound or a pharmaceutical composition as described above. In certain embodiments, the treated brain edema results from traumatic brain injury (TBI), a neurodegenerative disease or an acute or chronic challenge selected from infection, toxins, and excessive drug use of recreational, over the counter, and/or prescription drugs. Each possibility represents a separate embodiment of the present invention.

In an additional aspect, the present invention provides a method for promoting grafting or transplant of cells, tissues and/or organs, comprising the step of contacting such cells, tissues and/or organs with an effective amount of a compound or a pharmaceutical composition as described above. In one embodiment, the cells, tissues and/or organs are grafted or transplanted in a subject in need thereof. In one currently preferred embodiment, the cells, tissues and/or organs are grafted or transplanted in the CNS of a subject in need thereof. In one specific embodiment, the cells, tissues and/or organs are brain related. Each possibility represents a separate embodiment of the present invention.

In an additional embodiment, the present invention further provides a method for promoting brain development in a subject having a developmental disorder or who is at risk for having a developmental disorder, comprising the step of administering to a subject in need thereof an effective amount of a compound or a pharmaceutical composition as described above.

In certain embodiments, the developmental disorder is selected from the group consisting of Huntington disease, trisomy 21, Fragile X syndrome, Rett syndrome, Williams syndrome, pediatric autoimmune neuropsychiatric disorders associated with Streptococcal infection, Sydenham's chorea, toxoplasmosis, neurosyphilis, subacute sclerosing panencephalitis, schizophrenia, autism or developmental disorders caused by blindness, deafness, (sensory deprivation), metabolic disorders (e.g. diabetes, phenylketonuria), nutritional deficits (e.g. spina bifida, anencephaly, fetal alcohol syndrome), congenital injury or injury occurring in infancy or childhood. Each possibility represents a separate embodiment of the present invention.

In other embodiments, the present invention provides a method for repairing lesions and/or stimulating repair of the spinal cord by inducing axon growth across damaged areas and into their target area, comprising the step of administering to a subject in need thereof an effective amount of a compound or a pharmaceutical composition as described above.

In another aspect, the present invention provides a method for preventing or treating a cardiovascular disease, comprising the step of administering to a subject in need thereof an effective amount of a compound or a pharmaceutical composition as described above. In one preferred embodiment, the cardiovascular disease results from or is associated with Huntington Disease. In other embodiments, the cardiovascular disease is selected from the group consisting of heart failure, congestive heart failure, cardiac arrest, and myocardial infarction. Each possibility represents a separate embodiment of the present invention.

In certain embodiments, the compound or composition is administered prophylactically to a subject who is at risk of developing brain damage and/or neurodegeneration. In some embodiments, said subject is at risk for sustaining brain injury or for developing a neurodegenerative disease, brain edema or a cardiovascular disease, or the subject is a transplant candidate. According to other embodiments, the compound or composition is administered prophylactically to a subject selected from the group consisting of: a subject engaging in high risk activities, an infant or child at risk for developing a neurodevelopmental disorder associated with brain damage and/or neurodegeneration, a subject at risk for having a hereditary disease associated with brain damage and/or neurodegeneration, and a subject at risk for developing age related neurological diseases associated with brain damage and/or neurodegeneration. Each possibility represents a separate embodiment of the present invention.

The present invention further relates to the use of any one of the compounds or pharmaceutical composition as described above for the treatment or prevention of brain damage and/or progression and/or symptoms thereof.

The present invention further relates to the use of any one of the compounds or pharmaceutical composition as described above for preventing, reducing or treating CNS damage by activating migration, proliferation, adhesion, and/or differentiation, to thereby replenish depleted brain cells in a subject having brain damage due to injury or who is at risk for developing brain damage due to injury.

In another aspect, the present invention relates to the use of any one of the compounds or pharmaceutical composition as described above for treating or preventing a neurodegenerative disease or a symptom thereof.

In a particular aspect, the present invention relates to the use of any one of the compounds or pharmaceutical composition as described above for preventing programmed cell death in a subject having a neurodegenerative disease, or who is at risk for developing a neurodegenerative disease.

In a further aspect, the present invention relates to the use of any one of the compounds or pharmaceutical composition as described above for preventing, reducing or treating CNS damage by activating migration, proliferation, adhesion, and/or differentiation, to thereby replenish depleted brain cells in a subject having a neurodegenerative disease, or who is at risk for developing a neurodegenerative disease.

In another aspect, the present invention further relates to the use of any one of the compounds or pharmaceutical composition as described above for stimulating or enhancing restorative processes in the CNS, including migration of progenitor cells to damaged brain areas, neurodifferentiation in damaged brain areas, and re-establishment of damaged neurocircuitry.

In yet another aspect, the present invention further relates to the use of any one of the compounds or pharmaceutical composition as described above for treating or preventing brain edema.

In an additional aspect, the present invention relates to the use of any one of the compounds or pharmaceutical composition as described above for promoting grafting or transplant of cells, tissues and/or organs.

In another aspect, the present invention relates to the use of any one of the compounds or pharmaceutical composition as described above for promoting brain development in a subject having a developmental disorder or who is at risk of having a developmental disorder.

In an additional aspect, the present invention further relates to the use of any one of the compounds or pharmaceutical composition as described above for repairing lesions and/or stimulating repair of the spinal cord by inducing axon growth across damaged areas and into their target area in a subject in need thereof.

In yet another aspect, the present invention relates to the use of any one of the compounds or pharmaceutical composition as described above for treating or preventing a cardiovascular disease entailing heart failure. In a preferred embodiment, the described cardiovascular disease results from or is associated with Huntington Disease.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A: cell death induced by glutamate is dose dependently reduced by Cpd 1. Importantly, Cpd 1 has only very little lethal effect by itself. ###$p<0.001$ vs. vehicle control (control), * $p<0.05$ vs. glutamate exposed (glu), * $p<0.001$ vs. glutamate exposed cells (glu). FIG. 1B: $\Delta\Psi m$ collapse induced by glutamate is prevented by Cpd 1. ##$p<0.01$ vs. vehicle control (cont),  $p<0.01$ vs. glutamate exposed (glut); FIG. 1C: ROS generation at mitochondrial levels induced by glutamate is attenuated by Cpd 1. ###$p<0.001$ vs. vehicle control (cont), *** $p<0.001$ vs. glutamate exposed cells (glut).

FIG. 8: Protection against cell death induced by glutamate in U118MG cells by compounds 1, 5, 6, 7, 8 of the present invention.

DETAILED DESCRIPTION OF THE PRESENT INVENTION

Figure 1:
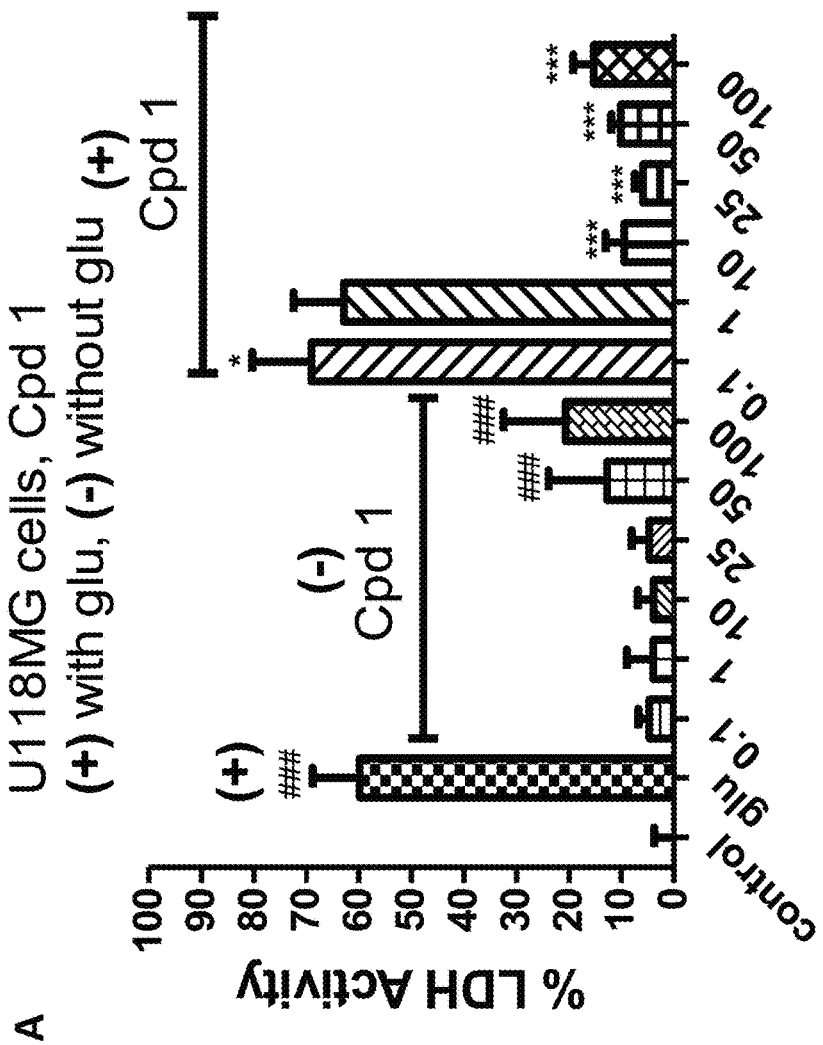
FIG. 1: Compound 1 (Cpd 1) (characterized by methyl and ethyl as alkyl groups) significantly reduces glutamate-induced cell death levels in culture of U118MG cells of neural origin (glutamate can act as a neurotoxin that has cell damaging effects in case of brain injury and neurodegeneration). This protection includes cell death processes under the control of the TSPO i.e. collapse of the mitochondrial potential ($\Delta\Psi m$) and cardiolipin oxidation are prevented.

The present invention relates to novel heterocyclic compounds including a quinazoline scaffold preferably having a set of asymmetric alkyl chains attached to the amide group of formula (I), and/or various halogens attached to the rotatable phenyl ring in formula (I), as well as individual compounds represented by the structure of formulas 1, 2, 3, 4, 5, 6, 7 and 8, as described herein. Compounds of the invention, in particular compound 1, bind effectively to the TSPO and regulate its cell death function, and may also regulate the role of TSPO role in gene expression, cell cycle, migration, proliferation, differentiation, and related tissue development and repair. The invention includes the pharmaceutical compositions containing the compounds, and their therapeutic use in treating and preventing brain damage resulting from acute events [e.g., traumatic brain injuries (TBI) and its after effects], chronic events (e.g., infection, toxins and/or drug use), and neurodegenerative diseases, and associated disorders.

Compounds

In one embodiment, the present invention provides a compound represented by the structure of formula (I):

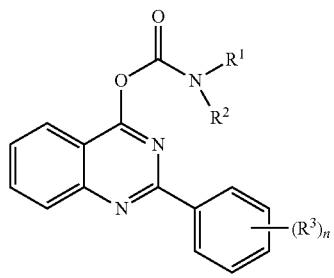

wherein $R^1$ and $R^2$ are each independently a linear or branched $C_1$-$C_{12}$ alkyl;

$R^3$ is a halogen; and n is 0, 1, 2, 3, 4 or 5;

with the proviso that, when n is 0, $R^1$ is different from $R^2$;

including salts, solvates, polymorphs, and mixtures thereof.

In one embodiment, $R^1$ and $R^2$ are each a $C_1$-$C_4$ alkyl. In some currently preferred embodiments, the compound is represented by the structure of formula (I), wherein $R^1$ and $R^2$ are each independently selected from the group consisting of methyl, ethyl, propyl, isopropyl, n-butyl, sec-butyl, isobutyl and tert-butyl.

In another currently preferred embodiment, the compound is represented by the structure of formula (I), wherein $R^1$ and $R^2$ are the same (thereby forming a symmetric amide), and n is other than 0. In another currently preferred embodiment, the compound is represented by the structure of formula (I), wherein $R^1$ and $R^2$ are different from each other (thereby forming an asymmetric amide). According to the principles of the present invention, when n is 0 (i.e. $R^3$ does not exist), $R^1$ and $R^2$ are different from each other. However, for halogenated derivatives in which n is other than 0, then $R^1$ and $R^2$ may be the same (symmetric amides) or different from each other (asymmetric amides).

In one preferred embodiment, n in the compounds of formula (I) is 0. In another preferred embodiment, n in the compounds of formula (I) is 1. In another preferred embodiment, n in the compounds of formula (I) is 2. Other possibilities include n is 3, 4, or 5. Currently preferred $R^3$ groups are Cl, Br or F, or a combination thereof. Each possibility represents a separate embodiment of the present invention. Representative compounds of the invention are selected from compounds 1, 2, 3, 4, 5, 6, 7, and 8 and are presented below.

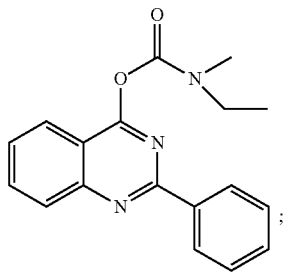

-continued

1
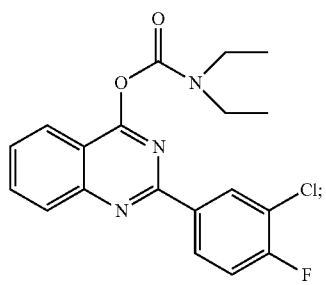

3
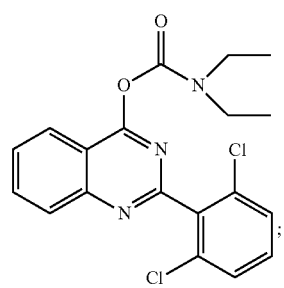

4
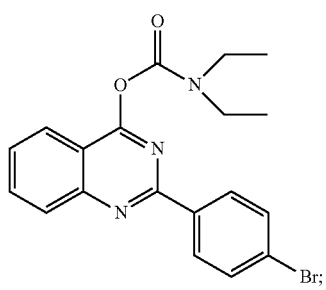

5
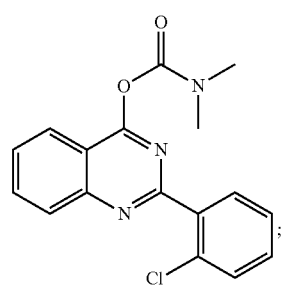

6
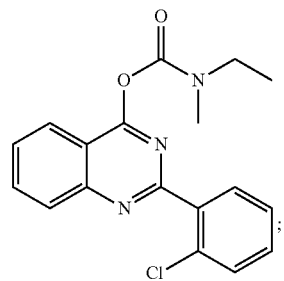

2
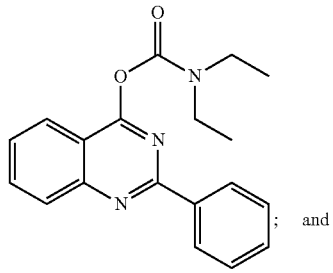
; and

8
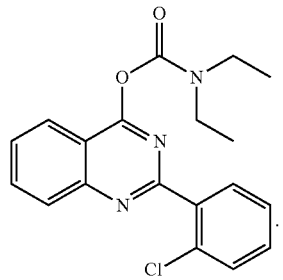

In one embodiment, it has been unexpectedly discovered that increasing the chain length of the amide moiety of compounds of formula (I) substantially increases the binding affinity to the TSPO. Thus, in one embodiment, compounds of the present invention wherein $R^1$ and $R^2$ are each independent alkyl groups of $C_2$-$C_{12}$ are currently preferred.

In another embodiment, it has unexpectedly been discovered that a compound comprising an asymmetric amide is more potent than its counterparts having symmetric amides. Thus, in one embodiment, compounds of formula (I) wherein $R^1$ is different from $R^2$ are currently preferred.

In another embodiment, it has unexpectedly been discovered that incorporation of halogen(s) on the rotatable phenyl ring prevents or reduces undesired lethal effects in cell culture induced by high concentrations of compound of the same structure but lacking the halogenation. Thus, in one embodiment compounds of formula (I) which contain one or more halogens on the phenyl ring are currently preferred.

Combinations of the above attributes are also contemplated, and represent another embodiment of the present invention. For example, compounds containing an asymmetric amide and a halogenated phenyl ring (e.g., compound 6) represent a preferred embodiment of the present invention.

In one embodiment, the present invention provides a pharmaceutical composition comprising a pharmaceutically acceptable carrier, and as an active ingredient a compound represented by formula (I) or selected from any one of compounds 1, 2, 3, 4, 5, 6, 7 and 8.

Chemical Definitions

The term "alkyl" as used herein refers to any saturated aliphatic hydrocarbon, including straight-chain and branched-chain groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. Examples of alkyl groups include, but are not limited to, methyl, ethyl, n-propyl, isopropyl, n-butyl, iso-butyl, sec-butyl, tert-butyl, pentyl including all its isomers, hexyl including all its isomers, heptyl including all its isomers, octyl including all its isomers, nonyl including all its isomers, decyl including all its isomers, undecyl including all its isomers, and dodecyl including all its isomers. Similarly, the term "alkylene" denotes a bivalent radical where the alkyl radical is bonded at two positions connecting together two separate additional groups (e.g., $CH_2$).

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{12}$ alkylthio arylthio, or $C_1$ to $C_{12}$ alkylsulfonyl groups. Any substituent can be unsubstituted or further substituted with any one of these aforementioned substituents.

The term "halogen" as used herein alone or as part of another group refers to chlorine (Cl), bromine (Br), fluorine (F), and iodine (I).

One or more of the compounds of the invention, may be present as a salt. The term "salt" encompasses both basic and acid addition salts, including but not limited to salts of amine nitrogens with organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The present invention also includes solvates of compounds of formula (I) and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates, and the like. "Hydrate" is a solvate wherein the solvent molecule is water.

The present invention also includes polymorphs of compounds of formula (I) and salts thereof. The term "polymorph" refers to a particular crystalline state of a substance, which can be characterized by particular physical properties such as X-ray diffraction, IR spectra, melting point, and the like.

Therapeutic Use

Glia constitutes the vast majority of brain cells and serves to maintain and protect healthy neurons, and it is now realized that glia presents a critical factor in the progress of neurodegeneration. The present invention is the first to actually consider glia, including astroglia, microglia, and oligodendrocytes, as a major venue for treatment of brain damage due to injury and disease.

Moreover, collapse of the mitochondrial membrane potential ($\Delta\Psi m$) appears to take a central role among the factors leading to neuronal cell death with secondary brain injury and neurodegenerative diseases. This suggests that targeting the regulation of the $\Delta\Psi m$, immediately after sustained brain injury, would have significant therapeutic implications for TBI. As TSPO is a major component for these mechanisms, the present invention targets the TSPO to treat brain damage associated with any type of brain injury, neurodegenerative diseases, and related conditions.

In a preferred embodiment, the compounds of the invention bind effectively to TSPO in combination with the prevention of cell death in a way superior to present day available treatments, including prevention of programmed cell death, as it occurs due to brain injury and/or neurodegenerative diseases.

Furthermore, the capability of the compounds of the invention to activate and facilitate repair properties regarding immune response, inflammation, cell proliferation, cell migration, cell differentiation, neurite outgrowth, etc., enables application for curative treatment of various types of brain damage, as described above and also due to excessive drug use, toxic challenges, infections, etc.

As mentioned above, the compounds of the invention prevent/reduce basal programmed cell death levels in neural cells i.e. glia and/or neurons, including attenuation of cell death induced by glutamate, which is known to be an important agent in processes underlying neurodegeneration and cell death and cell damage in the brain. Furthermore, these compounds prevent/reduce cell death induction by other agents that contribute to neurodegeneration and progression of brain damage. Thus, the compounds of the invention prevent cell death due to most if not all of the factors contributing to neurodegeneration, progressing brain trauma, and associated disorders. In addition, the compounds may contribute to repair of damaged brain areas by replenishing the damaged brain areas and re-establish damaged neurociruitry with new brain cells, including neurons, and stimulate their differentiation. As such, the compounds of the invention are useful in preventing, treating, and in addition to symptom amelioration, potentially providing actual cures for neurodegenerative diseases and progressing brain damage after brain injury.

The compounds of the invention provide better protection than classical TSPO ligands against programmed cell death. Furthermore, in contrast to problems seen with classical TSPO ligands in cell culture, the compounds of the invention are not as toxic at high concentrations, or not toxic at all. Furthermore, the compounds of the invention do not enhance apoptotic levels of apoptosis inducers such as glutamate, as classical TSPO ligands may do (in particular at high concentrations ≥50 μM) in cell culture. As such, the compounds of the invention are particularly advantageous as compared with classical TSPO ligands. In addition, they unexpectedly combine effective affinity to the TSPO with cell protective capacity, as compared with the compounds disclosed in U.S. Pat. No. 8,541,428. Furthermore, in an animal model (R6-2 mice) of Huntington Disease, the compounds of the present invention (e.g. compound 1) demonstrate favorable properties such as enhanced lifespan and increased locomotor activity, while classical TSPO ligands, and compounds disclosed in U.S. Pat. No. 8,541,428, completely lack these positive effects in the R6-2 model. It was further found in a separate experiment that compound 5 and compound 6 reduced the incidence of tremor activity. These characteristics indicate that the compounds have substantial neuroprotective properties, including the pathological behavioral effects and other symptoms, including lethality, and thus can be used to treat and prevent secondary brain damage after brain injury, brain surgery, neurodegenerative diseases, and associated disorders, for example, brain damage due to infections, toxic challenges, and excessive drug use, including recreational, over the counter, and prescribed drugs.

The compounds of the invention unexpectedly combine good affinity to the TSPO with very effective capability to reduce cell death levels in cells, in particular reduction of cell death levels by neurotoxic agents that are known to be an important agents causing secondary brain damage after traumatic brain injury, and also take part in neurodegenerative diseases. Furthermore, halogen(s) on the rotatable phenyl ring prevents or reduces undesired lethal effects in cell culture otherwise induced by high concentrations (100 μM) of compound of the same structure but lacking the halogenation. In these aspects the compounds of the invention are superior to known TSPO ligands. They are also superior to any compound presently available to treat such disorders. As such, the compounds of the invention are useful in the treatment and prevention of brain damage of any type, including brain damage resulting from traumatic brain injury (TBI), and/or secondary brain injury due to TBI as associated with, e.g., warfare, terrorism, traffic accidents (e.g., motor and non-motor vehicle accidents, and the like), sports injuries, violent crimes, household accidents, child abuse, domestic violence, work related accidents, gunshot wounds, etc. Other types of brain injury may be due to toxic challenges, infections of any kind, and excessive drug use including recreational, over the counter, or prescription drugs. The compounds can also be applied prophylactically in high risk situations associated with brain injury. The compounds of the invention are also useful in treating and preventing neurodegenerative diseases such as Alzheimer Disease, Parkinson Disease, Huntington disease, Lou Gehrig Disease, Multiple Sclerosis, autoimmune disorders, and others. Additional therapeutic indications are described hereinbelow.

Neurodegeneration and Neurodegenerative Diseases

In one aspect, the present invention provides a method for treating or preventing a neurodegenerative disease or a symptom thereof, comprising the step of administering to a subject in need thereof an effective amount of a compound of the present invention as described herein, or a pharmaceutical composition comprising such compound. In other embodiments, the present invention relates to use of any one of the compounds or pharmaceutical composition as described above in treating or preventing neurodegenerative diseases or a symptom thereof.

In another aspect, the present invention provides a method for preventing neurodegeneration (e.g. by preventing cell apoptosis) in a subject with a neurodegenerative disease or a subject who is at risk for developing a neurodegenerative disease, comprising the step of administering to a subject in need thereof an effective amount of a compound of the present invention, as described herein. In other embodiments, the present invention relates to use of any one of the compounds or pharmaceutical composition as described above in preventing neurodegeneration (e.g. by preventing cell apoptosis) in a subject with a neurodegenerative disease or who is at risk for developing a neurodegenerative disease.

In another aspect, the present invention provides a method for preventing, reducing or treating CNS damage, by activating and facilitating replenishment of lost brain cells via the processes of migration, proliferation, differentiation and/or adhesion of the required cells into and in the CNS regions in question, as well as other required regulation of immune response and inflammation. The method comprises the step of administering to a subject in need thereof an effective amount of a compound of the present invention, as described herein, or a pharmaceutical composition comprising such compound. The present invention further relates to the use of any one of the compounds or pharmaceutical composition as described above for preventing, reducing or treating CNS damage by activating migration, proliferation, adhesion and/or differentiation, to thereby replenish depleted brain cells in a subject in need thereof. In some embodiment, the subject has a neurodegenerative disease or is at risk for developing a neurodegenerative disease.

Generally, diseases of the central nervous system are referred to as neurodegenerative, indicating that they are characterized by gradually evolving, relentlessly progressive neuronal death occurring for reasons that are still largely unknown. As such, they are different from comparable conditions induced by infections, metabolic derangements, and intoxications. A considerable proportion of the disorders classed as neurodegenerative are genetic, with either dominant or recessive inheritance. Others, however, occur only sporadically as isolated instances in a given family, for which a cause is typically unknown. Classification of the degenerative diseases cannot be based upon any exact knowledge of cause or pathogenesis; their subdivision into individual syndromes rests on descriptive criteria based largely upon neuropathologic and clinical aspects. This group of diseases presents several distinct clinical syndromes, the recognition of which can assist the clinician in arriving at a diagnosis. The compounds of the invention are designed to treat any form of brain damage, be it due to mechanical injury, disease, infections, toxic challenges, and excessive use of drugs including recreational, over the counter, or prescription drugs, or otherwise.

Examples of neurodegenerative diseases in the context of the present invention include, but are not limited to, Alzheimer Disease, Parkinson Disease, Huntington Disease, Lou Gehrig Disease, Multiple Sclerosis, autoimmune disorders, Pick Disease, diffuse Lewy body Disease, progressive supranuclear palsy (Steel-Richardson syndrome), multisystem degeneration (Shy-Drager syndrome), motor neuron diseases, amyotrophic lateral sclerosis, degenerative ataxias, cortical basal degeneration, ALS-Parkinson-Dementia complex of Guam, subacute sclerosing panencephalitis, synucleinopathies, primary progressive aphasia, striatonigral degeneration, Machado-Joseph disease/spinocerebellar ataxia type 3 and olivopontocerebellar degenerations, Gilles De La Tourette Disease, bulbar and pseudobulbar palsy, spinal and spinobulbar muscular atrophy (Kennedy Disease), primary lateral sclerosis, familial spastic paraplegia, Werdnig-Hoffmann Disease, Kugelberg-Welander Disease, Tay-Sach Disease, Sandhoff Disease, familial spastic disease, Wohlfart-Kugelberg-Welander Disease, spastic paraparesis, progressive multifocal leukoencephalopathy, prion diseases, including Creutzfeldt-Jakob Disease, Gerstmann-Straussler-Scheinker Disease, Kuru, and fatal familial insomnia.

Brain Injury and Brain Damage

In another aspect, the present invention provides a method for treating or preventing brain damage and/or progression and/or symptom thereof, comprising the step of administering to a subject in need thereof an effective amount of a compound or composition of the present invention, as described herein. In some embodiments, the brain damage is due to brain injury resulting from an acute event, such as traumatic brain injury (TBI) and the subsequent progressing secondary brain injury resulting from TBI. In some aspects, the present invention provides a method for preventing or treating progression of brain damage resulting from traumatic brain injury (TBI) or secondary brain damage resulting from TBI, by activating and facilitating replenishment of lost brain cells and reestablishment of neurocircuitry via the processes of migration, proliferation, differentiation, and adhesion of the required cells into the CNS regions in question, as well as other required regulation of immune response and inflammation. The method comprises the step of administering to a subject in need thereof an effective amount of a compound of formula of the present invention as described herein.

The present invention also relates to the use of a compound of the present invention, in the manufacture of a medicament for treating or preventing brain damage and/or symptoms and/or progression of brain damage. The brain damage can be caused, e.g., by any type of brain injury.

In another aspect, the present invention further provides a method for preventing, reducing or treating CNS damage by activating migration, proliferation, adhesion, and/or differentiation, to thereby replenish depleted brain cells in a subject having brain damage due to injury, or who is at risk for developing brain damage due to injury, by administering to the subject an effective amount of a compound or a pharmaceutical composition as described above.

In one embodiment, the brain injury is due to an acute event, e.g., traumatic brain injury (TBI). In another embodiment, the brain damage is secondary brain damage resulting from TBI, which presents a continuing, chronic process. In another embodiment, this relates to agents that are involved in secondary brain damage or neurodegeneration, such as glutamate, glutamate receptor ligands other than glutamate, hypoxia mimicking agents, nitric oxide generating agents, apoptosis inducing agents, steroids, ammonium chloride, toxic compounds, or agents which interfere with ATP production. In another embodiment, the brain damage is due to a chronic challenge such as infection, toxins, and excessive drug use of recreational, over the counter, and/or prescription drugs.

In one embodiment, the brain injury is traumatic brain injury (TBI). As contemplated herein, the compounds of the invention are particularly useful for preventing and treating secondary brain damage resulting from TBI. Thus, the compounds of the invention are useful, e.g., for treating soldiers in the battlefield, especially soldiers who have suffered TBI. For example, secondary brain damage due to TBI can be treated or prevented by administering the compounds of the invention to soldiers, for example by supplying paramedics and/or the soldiers in the battlefield or under threat/at the site of terrorist attack with the compounds of the invention, so that the compounds can be administered on site as soon as possible after the soldier has suffered TBI. The compounds of the invention are also useful for civilians who are victims of violent crimes, including but not limited to, terrorist attacks, and any other mishap that can cause brain damage. This may reduce the incidence of disability presently occurring in the aftermath of TBI suffered due to hostilities, including terrorist attacks, as well as other crimes, and accidents.

The utility of the compounds of the invention is not limited to violent crimes such as warfare and terrorist attacks. The compounds of the invention are also useful for individuals suffering from brain injury due to domestic occurrences, such as traffic accidents (e.g., motor and non-motor vehicle accidents, and the like), sports injuries, work related accidents, household accidents, child abuse, domestic violence, gunshot wounds, etc, including their consequences such events such as disability and epilepsy. In another embodiment, under certain conditions, the compounds may be given prophylactically for sports with a very high incidence of CNS damage.

In a related aspect, the present invention provides a method of stimulating or enhancing restorative processes in the CNS, including migration of progenitor cells to damaged brain areas, neurodifferentiation in damaged brain areas, and re-establishment of damaged neurocircuitry. The method comprises the step of administering to a subject in need thereof an effective amount of a compound of the present invention, as described herein. The present invention further relates to the use of any one of the compounds or pharmaceutical composition as described above for stimulating or enhancing restorative processes in the CNS.

Cardiovascular Diseases

Heart failure is a major cause of death in R6-2 mice, a mouse model of Huntington Disease. This phenomenon appears to be associated both with the genetic condition as well as the stress it entails. It has now been discovered that the compounds of the present invention prevent heart failure in R6-2 mice. Thus, in other aspects, the present invention provides a method for preventing or treating a cardiovascular disease, in particular heart failure, comprising the step of administering to a subject in need thereof an effective amount of a compound or a pharmaceutical composition as described above. In one preferred embodiment the cardiovascular disease results from or is associated with Huntington Disease. The present invention relates to the use of any one of the compounds or pharmaceutical composition as described above for treating or preventing a cardiovascular disease, in particular heart failure.

Other Therapeutic Indications

In one aspect, the present invention provides a method for preventing, reducing or treating brain edema, comprising the step of administering to a subject in need thereof an effective amount of a compound or a pharmaceutical composition as described above. The present invention further relates to the use of any one of the compounds or pharmaceutical composition as described above for treating or preventing brain edema. The brain edema may results from traumatic brain injury, a neurodegenerative disease and/or an acute or chronic challenge as described above.

In an additional aspect, the compounds of the present invention support replacement of diseased and damage tissue by grafts/transplants. In accordance with this embodiment, the present invention further provides a method for promoting grafting or transplant of cells, tissues and/or organs, by contacting such cells, tissues and/or organs with an effective amount of a compound or a pharmaceutical composition as described above. In one currently preferred embodiment, the grafted or transplanted cells' target area is the CNS. In one specific embodiment, the cells, tissues and/or organs are brain related. The present invention further relates to the use of any one of the compounds or pharmaceutical composition as described above for promoting grafting or transplant of cells, tissues and/or organs.

In an additional embodiment the present invention further provides a method for promoting brain development in a subject having a developmental disorder or who is at risk for having a developmental disorder, comprising the step of administering to a subject in need thereof an effective amount of a compound or a pharmaceutical composition as described above. The compound of the current invention can be used for treating developmental disorders, example of such developmental disorders in the context of the present invention include, but are not limited to: Huntington disease, trisomy 21, Fragile X syndrome, Rett syndrome, Williams syndrome, pediatric autoimmune neuropsychiatric disorders associated with Streptococcal infection, Sydenham's chorea, toxoplasmosis, neurosyphilis, subacute sclerosing panencephalitis, schizophrenia, autism or developmental disorders caused by blindness, deafness, (sensory deprivation), metabolic disorders (e.g. diabetes, phenylketonuria), nutritional deficits (e.g. spina bifida, anencephaly, fetal alcohol syndrome), congenital injury or injury occurring in infancy or childhood. The present invention further relates to the use of any one of the compounds or pharmaceutical composition as described above for promoting brain development in a subject having a developmental disorder or who is at risk of having a developmental disorder.

In other embodiments, the present invention provides a method for repairing lesions and/or stimulating repair of the spinal cord by inducing axon growth across damaged areas and into their target area, comprising the step of administering to a subject in need thereof an effective amount of a compound or a pharmaceutical composition as described above. The present invention further relates to the use of any one of the compounds or pharmaceutical composition as described above for repairing lesions and/or stimulating repair of the spinal cord.

As mentioned above, the compounds of the invention may be used in one or more of the following modes of action: 1) prophylactically; 2) counteracting progressing damage (e.g., brain damage) and disease (e.g., neurodegeneration); 3) stimulating self-repair; and 4) supporting replacement of diseased and damage tissue by grafts/transplants. Thus, in certain embodiments the compound or composition as described above is administered prophylactically to a subject who is at risk of developing brain damage and/or neurodegeneration. In some embodiments, said subject is at risk for sustaining brain injury or for developing a neurodegenerative disease, brain edema or a cardiovascular disease, or wherein the subject is a transplant candidate. According to some embodiments, the prophylactically administered compound or composition is given to a subject selected from the group consisting of: a subject engaging in high risk activities, an infant or child at risk for developing a neurodevelopmental disorder associated with brain damage and/or neurodegeneration, a subject at risk for having a hereditary disease associated with brain damage and/or neurodegeneration, and a subject at risk for developing age related neurological diseases associated with brain damage and/or neurodegeneration.

In one preferred embodiment of any of the aforementioned methods, the compound is represented by the structure of formula (I). In another preferred embodiment, the compound is represented by the structure of formula 1. In another preferred embodiment, the compound is represented by the structure of formula 2. In another preferred embodiment, the compound is represented by the structure of formula 3. In another preferred embodiment, the compound is represented by the structure of formula 4. In another preferred embodiment, the compound is represented by the structure of formula 5. In another preferred embodiment, the compound is represented by the structure of formula 6. In another preferred embodiment, the compound is represented by the structure of formula 7. In another preferred embodiment, the compound is represented by the structure of formula 8. Each possibility represents a separate embodiment of the present invention.

As used herein, the term "administering" refers to bringing in contact with a compound of the present invention. Administration can be accomplished to cells or tissue cultures, or to living organisms, for example humans. In one embodiment, the present invention encompasses administering the compounds of the present invention to a human subject.

A "therapeutic" or "effective" treatment is a treatment administered to a subject who exhibits signs of pathology for the purpose of diminishing or eliminating those signs. A "therapeutically effective amount" or an "effective amount" of a compound of the invention is that amount of compound which is sufficient to provide a beneficial effect to the subject to which the compound is administered. Examples of effective treatments according to the present invention include, but are not limited to, reducing or ameliorating one or more symptoms of TBI or any of the neurodegenerative diseases described herein, increasing lifespan, increasing motor activity, increasing cognitive capabilities and other brain functions, and preventing the progression of TBI and/or neurodegenerative diseases. Similarly, the compounds of the invention may be used to treat brain damage due to infections, toxic challenges, excessive drug use, being recreational, over the counter, or prescription, etc.

As used herein, the term "brain edema" refers to a condition of accumulation of excess fluid in the intracellular or extracellular spaces of the brain. Brain edema in the context of the present invention can be a result of a traumatic brain injury (TBI), a neurodegenerative disease or an acute or chronic challenge selected from infection, toxins, and excessive drug use of recreational, over the counter, and/or prescription drugs.

The terms "grafting" and "transplant" refer to a section of tissue or a complete organ that is removed from its original natural site and transferred to a new position in the same person or in a separate individual.

The term "cardiovascular disease" refers to heart and blood vessel disease. Cardiovascular disease in the context of the present invention includes, but is not limited to heart failure, congestive heart failure, cardiac arrest, and myocardial infarction.

Pharmaceutical Compositions

Although the compounds of the present invention can be administered alone, it is contemplated that these compounds will be administered in a pharmaceutical composition containing the compound of the invention together with a pharmaceutically acceptable carrier or excipient.

The pharmaceutical compositions of the present invention can be formulated for administration by a variety of routes including oral, rectal, transdermal, parenteral (subcutaneous, intraperitoneal, intravenous, intraarterial, transdermal, and intramuscular), topical, intranasal, rectally via a suppository, or via dialysis. Such compositions are prepared in a manner well known in the pharmaceutical art and comprise as an active ingredient at least one compound of the present invention as described hereinabove, and a pharmaceutically acceptable excipient or a carrier. The term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material. The compositions are preferably suited for oral administration, in which case they can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The carriers may be any of those conventionally used. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. Other pharmaceutical carriers can be sterile liquids, such as water, alcohols (e.g. ethanol) and lipid carriers such as oils (including those of petroleum, animal, vegetable or synthetic origin, such as peanut oil, soybean oil, mineral oil, sesame oil and the like), phospholipids (e.g. lecithin), polyethylene glycols, glycerine, propylene glycol, or other synthetic solvents. Water is a preferred carrier when the pharmaceutical composition is administered intravenously. Saline solutions and aqueous dextrose and glycerol solutions can also be employed as liquid carriers, particularly for injectable solutions.

The formulations can additionally include lubricating agents such as talc, magnesium stearate, and mineral oil; wetting agents, anti-oxidants, surfactants, emulsifying and suspending agents; preserving agents such as methyl- and propylhydroxybenzoates; sweetening agents; flavoring agents, colorants, buffering agents (e.g. acetates, citrates or phosphates), disintegrating agents, moistening agents, antibacterial agents, antioxidants (e.g. ascorbic acid or sodium bisulfite), chelating agents (e.g. ethylenediaminetetraacetic acid), and agents for the adjustment of tonicity such as sodium chloride. Fatty acids can also be included.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills, and capsules. This solid preformulation is then subdivided into unit dosage forms of the type described above containing from, for example, 0.1 to about 500 mg of the active ingredient of the present invention.

Any method can be used to prepare the pharmaceutical compositions. Solid dosage forms can be prepared by wet granulation, dry granulation, direct compression, and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, alcoholic solutions, suitably flavored syrups, aqueous or oil suspensions, and flavored emulsions with edible oils such as cottonseed oil, sesame oil, coconut oil, or peanut oil, as well as elixirs, and similar pharmaceutical vehicles.

Compositions for inhalation include solutions and suspensions in pharmaceutically acceptable aqueous or organic solvents, or mixtures thereof, and powders. The liquid or solid compositions may contain suitable pharmaceutically acceptable excipients as described above. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel, a drop, or a cream. For topical administration to body surfaces using, for example, creams, gels, drops, ointments, and the like, the compounds of the present invention can be prepared and applied in a physiologically acceptable diluent with or without a pharmaceutical carrier. Adjuvants for topical or gel base forms may include, for example, sodium carboxymethylcellulose, polyacrylates, polyoxyethylene-polyoxypropylene-block polymers, polyethylene glycol, and wood wax alcohols.

Alternative formulations include nasal sprays, liposomal formulations, immediate-release formulations, slow-release formulations, controlled-release formulations, delayed-release formulations and the like, as are known in the art.

The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than about 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, topical application, e.g. in conjunction with a wound dressing after surgery, by injection, by means of a catheter, by means of a suppository, or by means of an implant, said implant being of a porous, non-porous, or gelatinous material.

The compounds may also be administered by any convenient route, for example by infusion or bolus injection, by absorption through epithelial linings (e.g. oral mucosa, rectal and intestinal mucosa, etc.), and may be administered together with other therapeutically active agents. Administration may be localized, preferably close to the affected, injured, or diseased area, but it may also be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. A targeted drug delivery system can be used, including nanotechnology. Pulmonary administration can also be employed, e.g. by use of an inhaler or nebulizer, and formulation with an aerosolizing agent.

In one embodiment, an infusion pump may be used to administer a compound of the invention. Thus, a compound of the invention may be administered in combination with a biodegradable, biocompatible polymeric implant, which releases the compound over a controlled period of time at a selected site. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Furthermore, at times, the pharmaceutical compositions may be formulated for parenteral administration (subcutaneous, intravenous, intraarterial, transdermal, intraperitoneal, or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

The amount of a compound of the invention that will be effective in the treatment of a particular disorder or condition, including TBI, neurodegenerative diseases and other comparable disorders and injuries, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. A preferred dosage will be within the range of 0.01-1000 mg/kg of body weight, more preferably, about 0.1 mg/kg to about 100 mg/kg and even more preferably about 1 mg/kg to about 10 mg/kg. Effective doses may be extrapolated from dose-response curves derived from in vitro or animal model test bioassays or systems.

Synthetic Methods

Quinazoline derivatives of formula (I) can be prepared as described in Scheme 1 and as further detailed in Example 9.

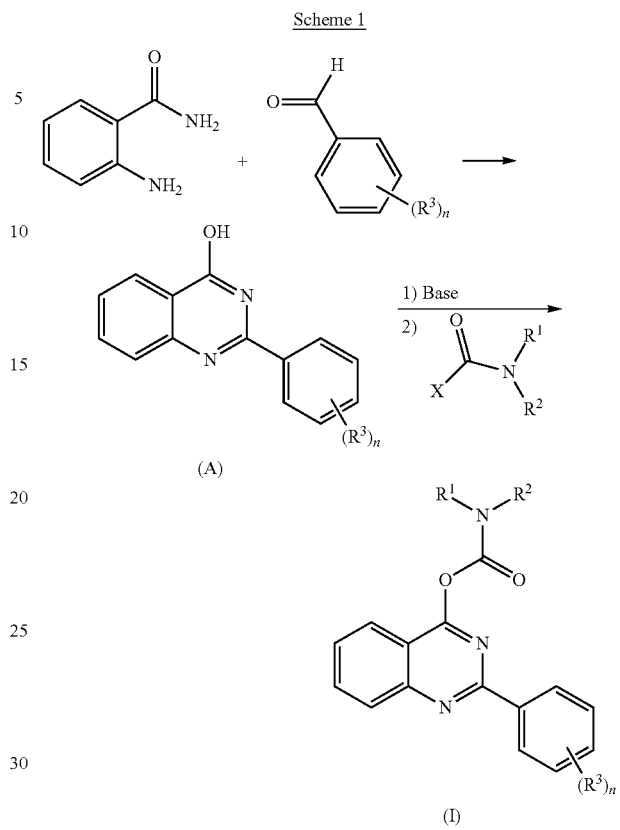

Scheme 1

In Scheme 1, $R^1$, $R^2$, $R^3$ and n are as defined above for Formula (I).

Commercially available anthranilamide reacts with benzaldehyde or a halogenated derivative thereof, to give 2-phenylquinazolin-4-ol or a halogenated derivative thereof (Intermediate A). The intermediate is treated with a base (e.g. a hydride such as sodium or potassium hydride) to prepare the corresponding alcoholate, followed by addition of a carbamoyl derivative (X is, e.g., a halogen, preferably Cl), to yield the O-amidation product. Different alkyl groups on the nitrogen atom of carbamoyl chloride can be prepared as desired.

The nature of the base is not particularly limiting. Preferred bases include, but are not limited to, hydrides (e.g. sodium or potassium hydride). Other suitable bases include, but are not limited to an organic base such as a tertiary amine selected from acyclic amines (e.g. trimethylamine, triethylamine, dimethylphenylamine, diisopropylethylamine and tributylamine), cyclic amines (e.g. N-methylmorpholine), and aromatic amines (e.g. dimethylaniline, dimethylaminopyridine, and pyridine).

The reaction may be conducted in the presence or absence of a solvent. The nature of the solvent, when used, is not particularly limiting, with examples including solvents such as esters (e.g. ethyl acetate), ethers (e.g. dimethoxyethane, THF), chlorinated solvents (e.g. dichloromethane or chloroform), dimethylformamide (DMF), acetonitrile or toluene, or mixtures of these solvents with each other.

In one embodiment, the base is potassium hydride (KH) and the solvent is dimethoxyethane (DME).

All references cited in the present application are expressly incorporated by reference in their entirety, as if fully set forth herein.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Experimental Details Section

Example 1—Materials and Methods for Biological Assays

TSPO Binding and Western Blot Protein Analysis

TSPO binding assays were utilized to determine whether the compounds of the invention are able to compete with standard TSPO ligands, according to methods described previously (Veenman et al. 2004; Levin et al. 2005), and are used for quality control. Briefly, the assay utilizes radioactive standard ligand [$^3$H] PK 11195 (1-(2-chlorophenyl)-N-methyl-N-(1-methyl-propyl)-3 isoquinolinecarboxamide), and measures the ability of the compounds of the invention to displace standard ligand in binding to TSPO. Total radioactive binding was determined by measuring the radioactivity of the radioactive ligand-receptor complex, obtained in the reaction of radioactive standard with the TSPO. Radioactive standard and the examined compound were added to the TSPO and after some incubation time the radioactivity of the resulting ligand-receptor complexes was measured with the help of a γ-counter. This radioactivity indicates the binding of the radioactive standard to TSPO. When the examined compound binds better to TSPO, consequently, less radioactive standard binds to TSPO, therefore the measured radioactivity is lower. This can be expressed as the half maximal inhibitory concentration (IC50), which is a measure of the effectiveness of a compound in inhibiting biological or biochemical function, in this case inhibiting binding of standard radioactive ligand binding to the TSPO. A derivative of the IC50 is the Ki, which is the calculated binding affinity of the novel compound to the TSPO.

Cell cultures of various human glial type cell lines (T98G, U87MG, A172, U118MG), as well as human neuronal type cell lines SH-SY 5Y and Be(2)-C were used to test the new compounds. In addition, the rat glioma cell line C6 was used. PC12 cells originating from rats were used as another cell line displaying neuronal characteristics. The applicants also have produced, by genetic manipulation, a modified rat C6 glial cell strain and a modified human U118MG glial type cell strain, both under-expressing the TSPO, which allows to study TSPO specific effects, including of the compounds of the invention, which can be done according to methods described previously (Weisinger et al. Biochemistry. 2004; 43:12315-21; Levin et al. 2005; Zeno et al., 2009).

The protective capabilities of the compounds of the invention and involvement of the TSPO were tested in cell culture, using cell lines of glial and neuronal type, cultured and testing according to standard methods (Kugler et al. 2008; Zeno et al. 2009; Dadon-Nachum et al. Stem Cell Rev. 2011; 7:664-71). Furthermore, primary cell cultures are also used (Banker, G. et al. Culturing Nerve Cells, 2nd Edition, The MIT Press (1998). Treatments included: (1) exposure to glutamate (35 mM), Abeta(1-42), $NH_4Cl$, $CoCl_2$, and nitric oxide (NO) donors, in order to mimic particular aspects of neurodegeneration; (2) treatment with the novel compounds and with traditional TSPO ligands as comparative treatment; and (3) TSPO knockdown by genetic manipulation.

Techniques and parameters assayed are summarized here: Total protein levels (Bradford. Anal Biochem. 1976; 72:248-54); TSPO ligand binding assays (Kugler et al. 2008; Levin et al. 2005; Danovich et al. Eur Neuropsychopharmacol. 2008; 18:24-33) cell death, including apoptosis and necrosis and related molecular biological processes (Soustiel et al. Neuropathol Appl Neurobiol. 2008; 34:412-23; Soustiel et al. Exp Neurol. 2008; 214:201-8; Zeno et al. 2009); mitochondrial transmembrane potential collapse (Chelli et al. Biochem Pharmacol. 2004; 68:125-34; Kugler et al. 2008; Zeno et al., 2009; Shargorodsky et al. Apoptosis. 2012; 17:647-65), reactive oxygen species (ROS) generation as a measure of oxidative stress (Veenman et al. 2008; Zeno et al. 2009); TSPO knockdown (Levin et al. 2005; Zeno et al. 2009); expression levels of mitochondrial TSPO and associated proteins (Veenman et al. 2002; Levin et al. 2005; Veenman et al. 2008); gene expression with RT-PCR and microarray analysis (Bode et al. 2012; Veenman et al. 2012). Parameters of inflammation, immune response, migration, and the cell cycle are also tested. All these approaches can also be applied for quality control of the compounds.

Data are expressed as means±SD or SEM as appropriate. One-way or multiple analysis of variance, including post-hoc tests, as appropriate, are used to analyze the data. Bartlett's test for homogeneity of variance is used to determine the appropriate model i.e. parametric or non-parametric. Statistical significance is defined at $p<0.05$.

Animal Studies

For the assays described herein systemic injections of kainic in rats were applied and also contusion (Veenman et al. 2002; Soustiel et al. Neuropathol Appl Neurobiol. 2008; Soustiel et al. Exp Neurol. 2008). These models present very well defined cell death in the brain. Cell death in the brain is the major pathological characteristic of progressing neurodegeneration common to brain diseases. As the compounds of the present invention are designed to prevent cell death in the brain as a consequence of disease and progressing brain damage after injury, including behavioral impairments, animal models displaying cell death in the brain are the models of choice for displaying the protective capabilities of the compounds of the invention. For these reasons the R6-2 model for Huntington Disease was chosen to test the effectiveness of Compound 1 and to compare the effectiveness of Compound 1 with those of the compound of U.S. Pat. No. 8,541,428 (Cpd A) and with the classical TSPO ligand PK 11195, as well as other compounds disclosed herein. Compounds 5 and 6 were also tested in the same R6-2 model.

Example 2: In Vitro Binding to TSPO

Binding to TSPO was evaluated using a [$^3$H]PK 11195 radio-assay, as described above.

Results of binding to TSPO and protective effects of the compounds of the present invention are provided in Table 1. Compounds 1-8 were tested in cell culture, and favored compounds also in animal models (i.e. Compound 1). The structures of these compounds are provided hereinabove. Table 1 also includes the compound encompassed by U.S. Pat. No. 8,541,428 (compound A).

TABLE 1

| Compound | Ki (nM) | Protection* |
|---|---|---|
| 1 | ≈ 60 | Excellent |
| 2 | ≈ 380 | Good |

TABLE 1-continued

| Compound | Ki (nM) | Protection* |
|---|---|---|
| 3 | ≈ 1506 | Good |
| 4 | ≈ 45 | Good |
| 5 | ≈ 600 | Excellent |
| 6 | ≈ 60 | Excellent |
| 7 | ≈ 2.5 | Good |
| 8 | ≈ 2.5 | Good |
| A | ≈ 600 | Good |

*Protection against glutamate-induced cell death

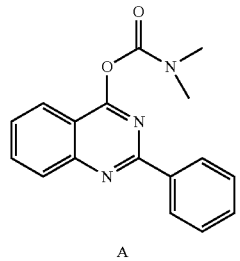

A

A comparison of Compound 1 of the present invention with Compound A, which is exemplified in U.S. Pat. No. 8,541,428, indicates that the nature of the alkyl groups on the N-amide moiety has a strong effect on the affinity of the compounds to TSPO, and most importantly that the asymmetric amide results in a combination of protective effects with relative high affinity to TSPO. Thus, without wishing to be bound by any particular mechanism or theory, it is believed that the asymmetry is beneficial for the combination of affinity to TSPO and the capability to protect the cells from cell death. This finding was completely unexpected and represents a separate embodiment of the present invention.

Figure 7:
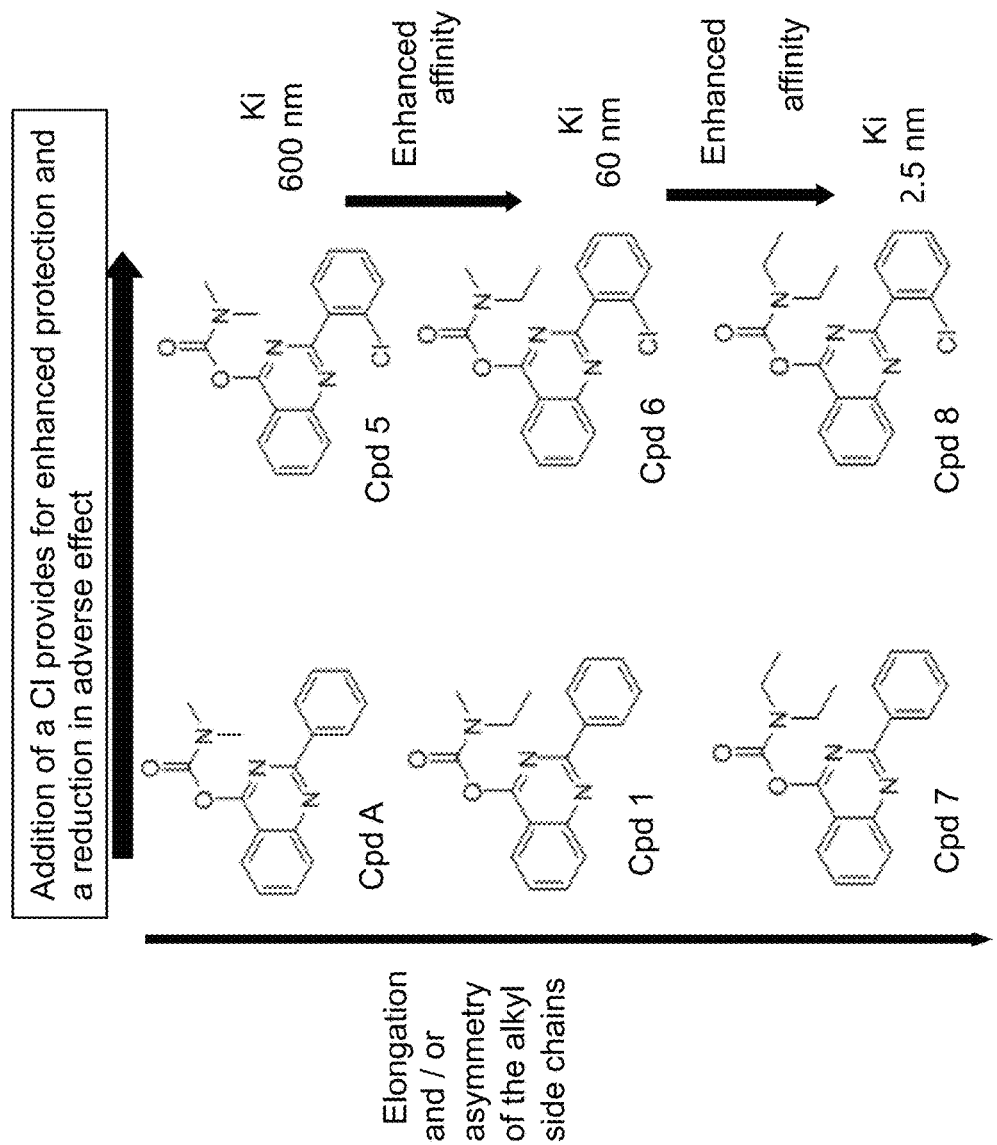
FIG. 7: Functional characteristics of compounds 1, 5, 6, 7, 8 of the present invention in comparison to compound A. "Moderate" affinity provided by alkyl modifications (Ki~60 nM) provides optimal protection (Cpd 1 and Cpd 6). Addition of halogen to the rotatable phenyl improves protection and reduces lethal effects at "high" concentrations (100 µM) (Cpd 5, 6, 8). Additional elongation of alkyl side chains provides relatively strong affinity for the TSPO (Cpd 7, 8). Production of derived compounds combining alkyl modifications and halogenation further enhances protective effects to glutamate, e.g., Cpd 6 in comparison to all other compounds in this scheme. For details, see FIGS. 8 and 9.
Figure 8B:
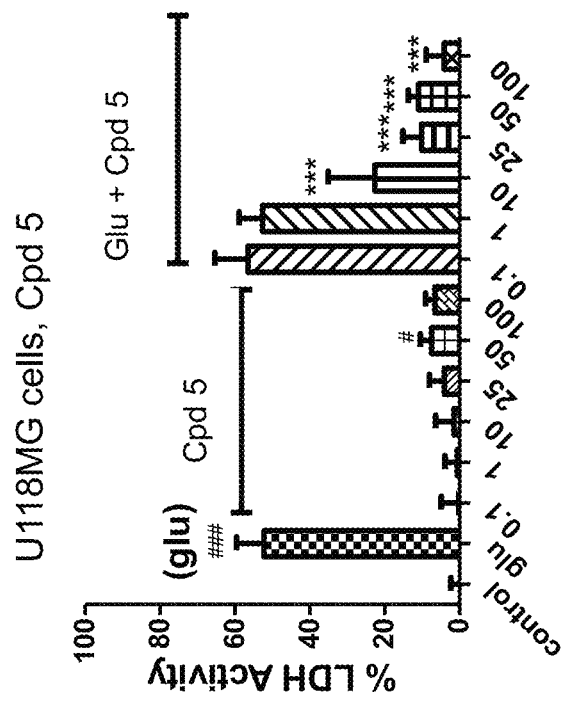
FIG. 8B: Cpd 5.
Figure 8A:
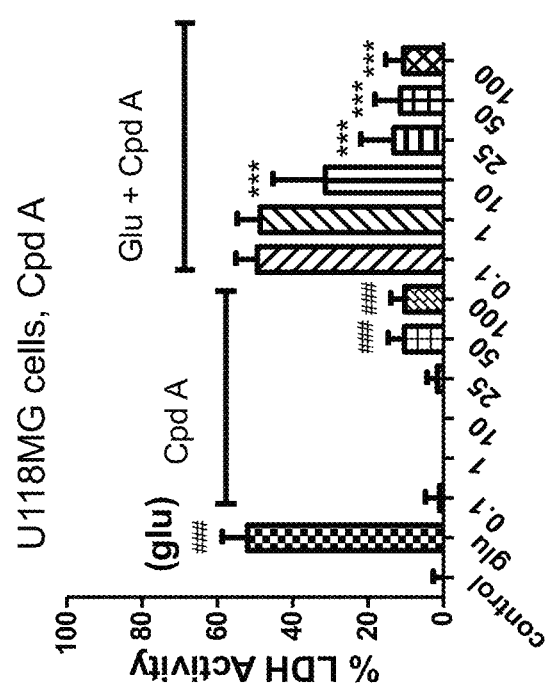
FIG. 8A: Reference Cpd A (U.S. Pat. No. 8,541, 428).
Figure 8D:
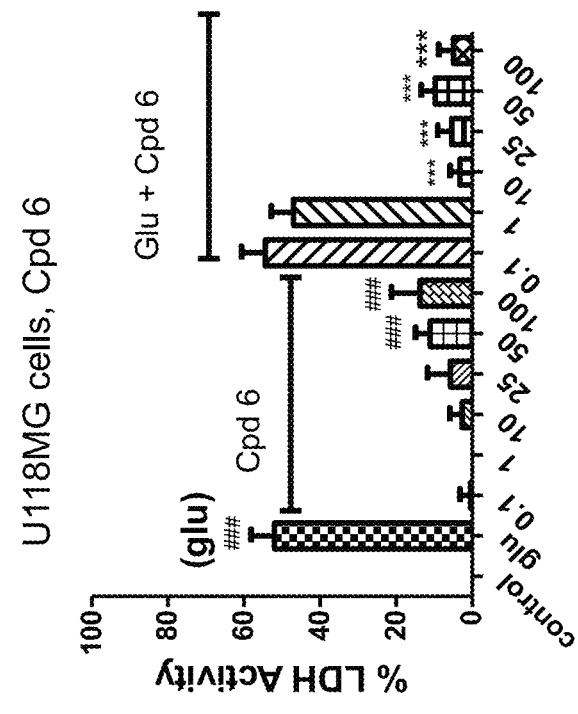
FIG. 8D: Cpd 6.
Figure 8C:
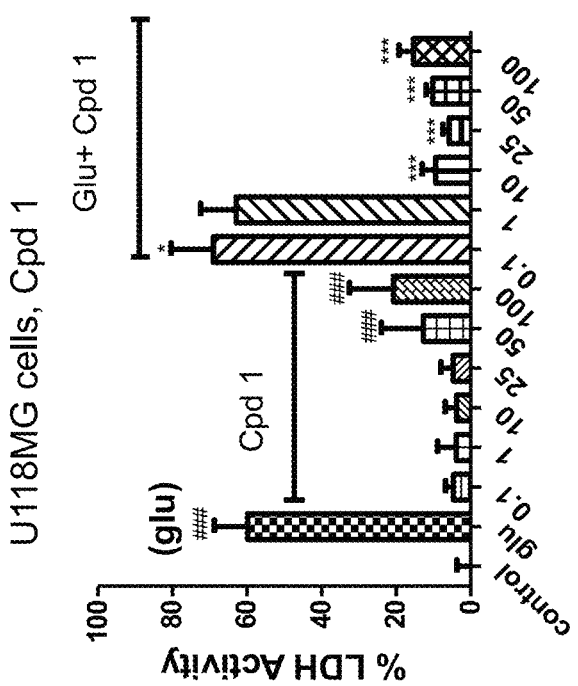
FIG. 8C (=FIG. 1A): Cpd 1.
Figure 8F:
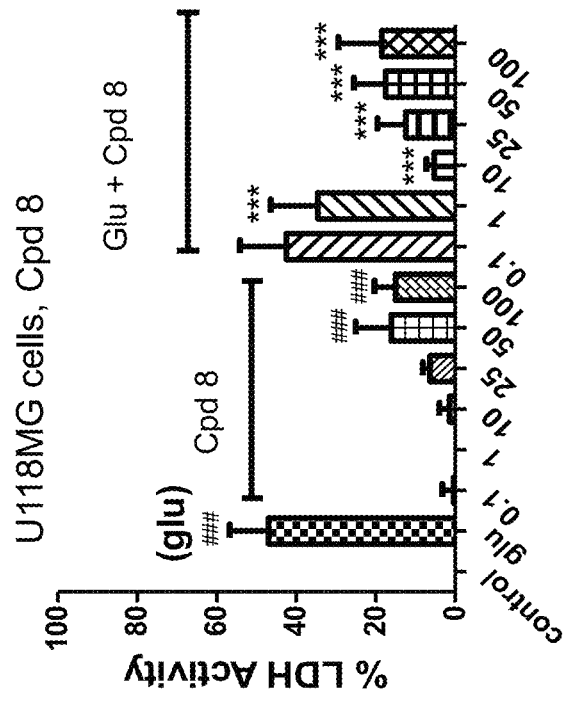
FIG. 8F: Cpd 8. #$p<0.05$ vs. vehicle control (control), ###p<0.001 vs. vehicle control (control), * p<0.05 vs. glutamate exposed (glu), *** p<0.001 vs. glutamate exposed cells (glu).
Figure 8E:
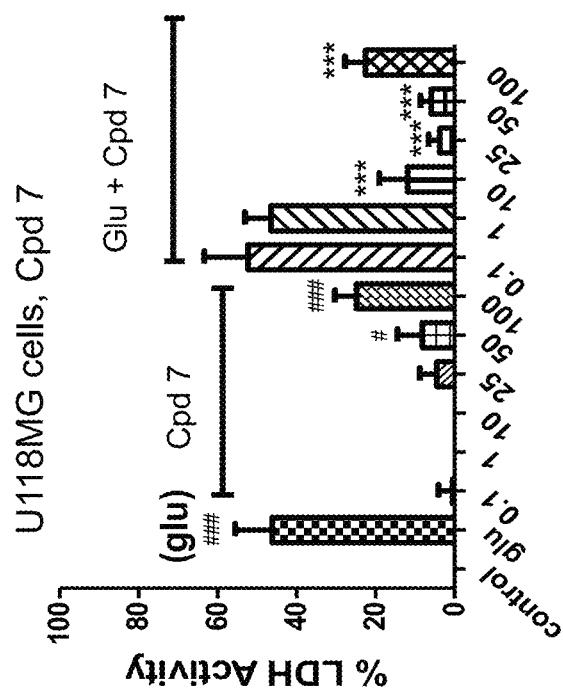
FIG. 8E: Cpd 7.
Figure 9A:
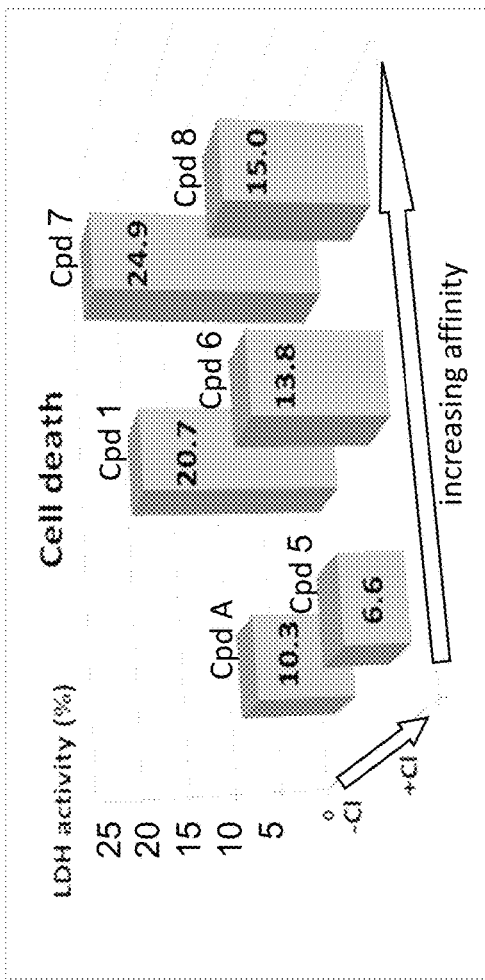
FIG. 9: Reduction of adverse, undesired cell death effects in culture. A comparative summary of the effects seen due to application of 100 μM (i.e. high concentration) of the compounds presented in FIGS. 7 and 8. Undesired lethal effects of the compounds of the invention are minimized by halogenation. This summary shows that halogenation with Cl reduces lethal effects at a concentration of 100 μM, i.e. only the protective characteristics remain. A) Halogenation of Cpd A, Cpd 1 and Cpd 7 to yield Cpd 5, Cpd 6, and Cpd 8 respectively, reduces cell death effects of this high concentration in cultures. B) The halogenated Cpd 5, Cpd 6, and Cpd 8 reduces cell death effect of glutamate in cultures even further than the corresponding unhalogenated Cpd A, Cpd 1, and Cpd 7 do. When unchecked, glutamate by itself typically kills 50-60% of the cells, but with even the suboptimal dose of 100 μM of Cpd 6 only 5% of the cells are killed by glutamate. From this presentation it can also be concluded that Cpd 5 shows the least adverse side effects.
Figure 9B:
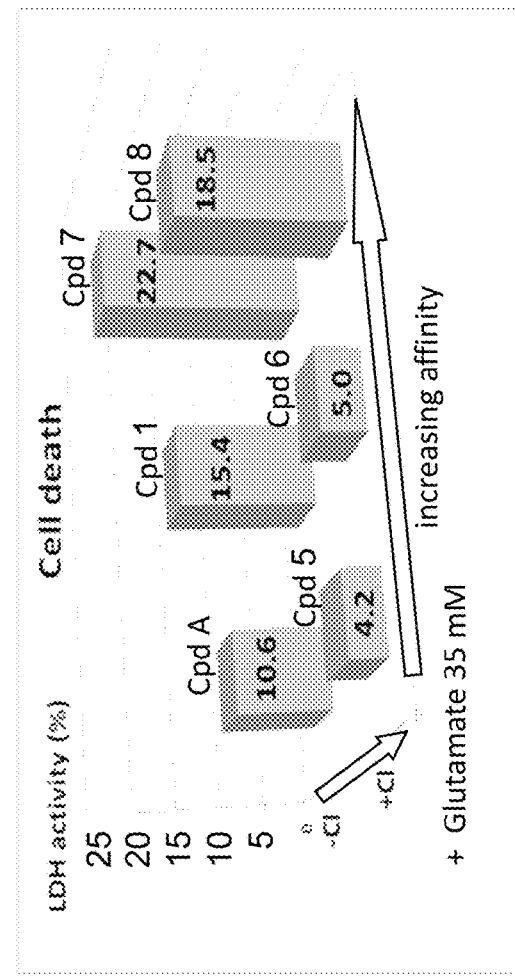

Furthermore, it has been discovered that halogens attached to the rotatable phenyl ring linked to the quinazoline scaffold appears to improve cell protective effects, while retaining TSPO binding affinity (FIGS. 2-4 and 7-9). It is therefore contemplated that attachment of halogen substituents to the compounds of formula (I) allows for further improvements, most notably regarding their capability to protect against cell death. FIGS. 7 to 9 show that halogenation at the phenyl ring does not necessarily affect TSPO affinity, but does have positive effects regarding protection. Thus, without wishing to be bound by any particular mechanism or theory, it is believed that halogenation may be beneficial for the capability of the compounds of the present invention to protect the cells from cell death. This additional finding was completely unexpected and represents a separate embodiment of the present invention.

Moreover, compounds having a combination of asymmetrical amides and halogenated rotatable phenyls may have enhanced properties, combining the advantages conferred by both the asymmetrical amide and the halogen components.

Example 3: Protective Properties of Compounds of the Invention

Figure 3:
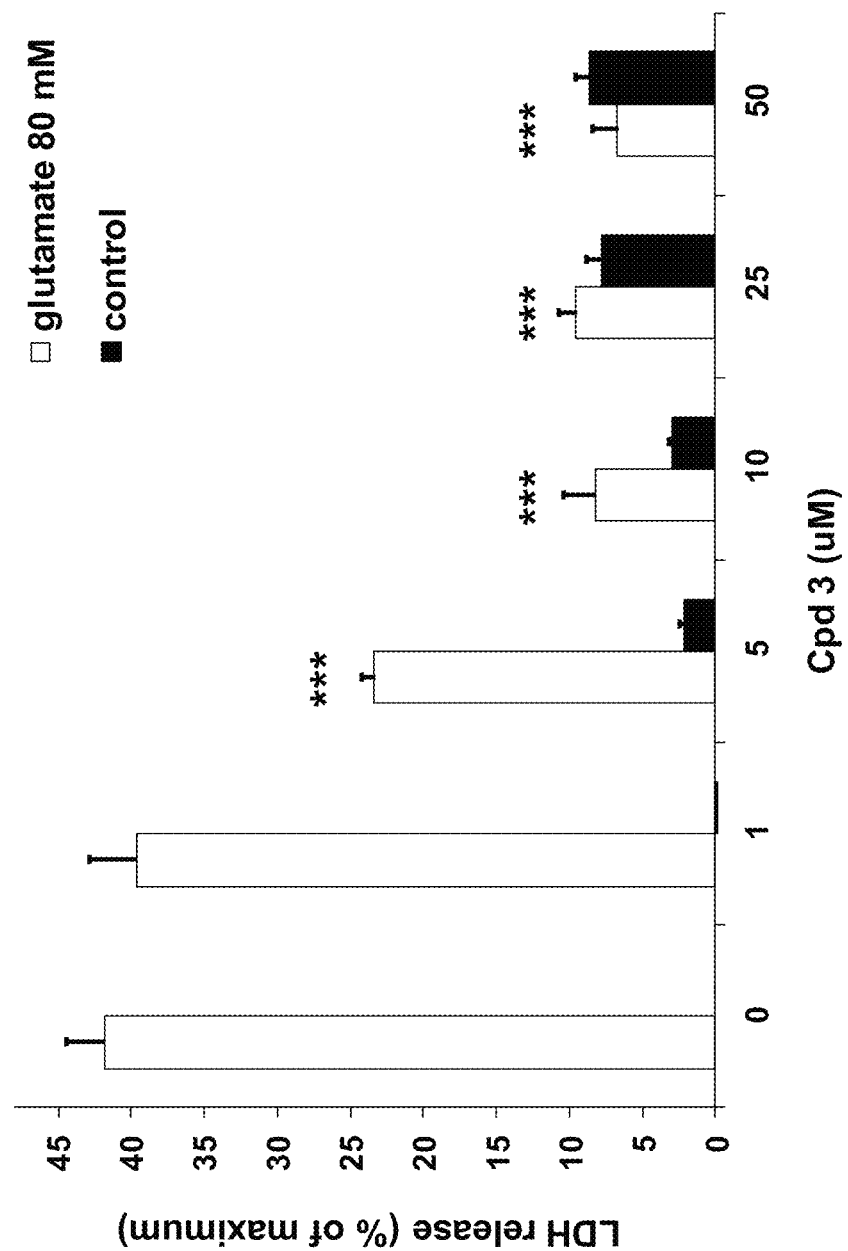
FIG. 3: shows protective properties of compound 3 (characterized by a rotatable phenyl ring halogenated with Cl at two positions) in vitro. n=4, results are depicted as average±SEM. ***: One way ANOVA gave $p<0.0001$; Bonferroni Multiple Comparisons Test gave $p<0.001$ for glutamate vs. glutamate+compound 3 (5-50 µM). The white columns present exposure to glutamate without (0) or with Cpd 3 (1, 5, 10, 25, 50 µM). The black columns present treatment with only Cpd 3.
Figure 4:
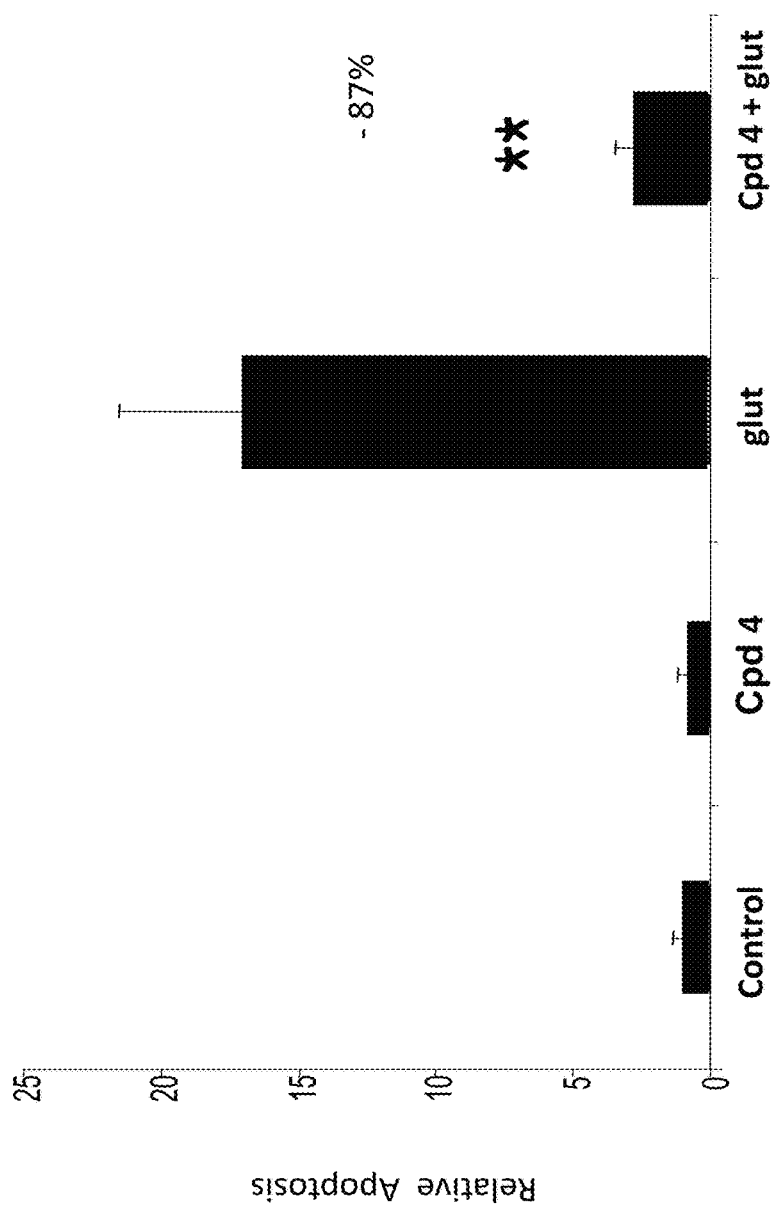
FIG. 4: Compound 4 (characterized by a rotatable phenyl ring halogenated with Br) protects neuronal cells from the SH SY 6Y cell line against lethal effects of glutamate in vitro. n=6, **=$p<0.01$ One way ANOVA with Mann-Whitney as posthoc. Control: no glutamate exposure and no Cpd 4 treatment. Cpd 4: only Cpd 4 treatment. Glut: only glutamate exposure. Cpd 4+glut: glutamate exposure together with glutamate treatment.

The compounds of the invention protect against cell death induced by glutamate in cell culture of U118MG cells of astrocytic origin (FIGS. 1, 2, 3 and 8) or SH SY 6Y cells of neuronal origin (FIG. 4). FIG. 1 shows that Compound 1, which has good affinity for the TSPO (Table 1), prevents cell death and cell death processes induced by glutamate. As shown in FIG. 1A, Compound 1 of the present invention protects against glial cell death induced by 35 mM of glutamate in cell culture (Results are depicted as AVG±SD).

In the control group, 35 mM of glutamate killed ~60% of the cells. Compound 1 at concentrations from 10-100 μM significantly protects against cell death induced by glutamate in glial cell culture. In comparison, prior art Compound A (U.S. Pat. No. 8,541,428) is unexpectedly significantly less efficacious at protecting against cell death (FIG. 8A). * $p<0.05$ vs. glutamate exposure (glu), *** $p<0.001$ vs. glu. ### $p<0.001$ vs. vehicle control (control), n=12 for each group Furthermore, as shown in FIG. 1B, Compound 1 prevents collapse of the mitochondrial membrane potential ($\Delta\Psi m$), which is typically induced by glutamate and is normally under control of the TSPO (Results are depicted as AVG±SD). Compound 1 is very effective at a concentration of 25 μM in this model (in order to achieve the same effect with the classical TSPO ligand PK 11195 a concentration of 50 μM has to be applied (data not shown).

Figure 2:
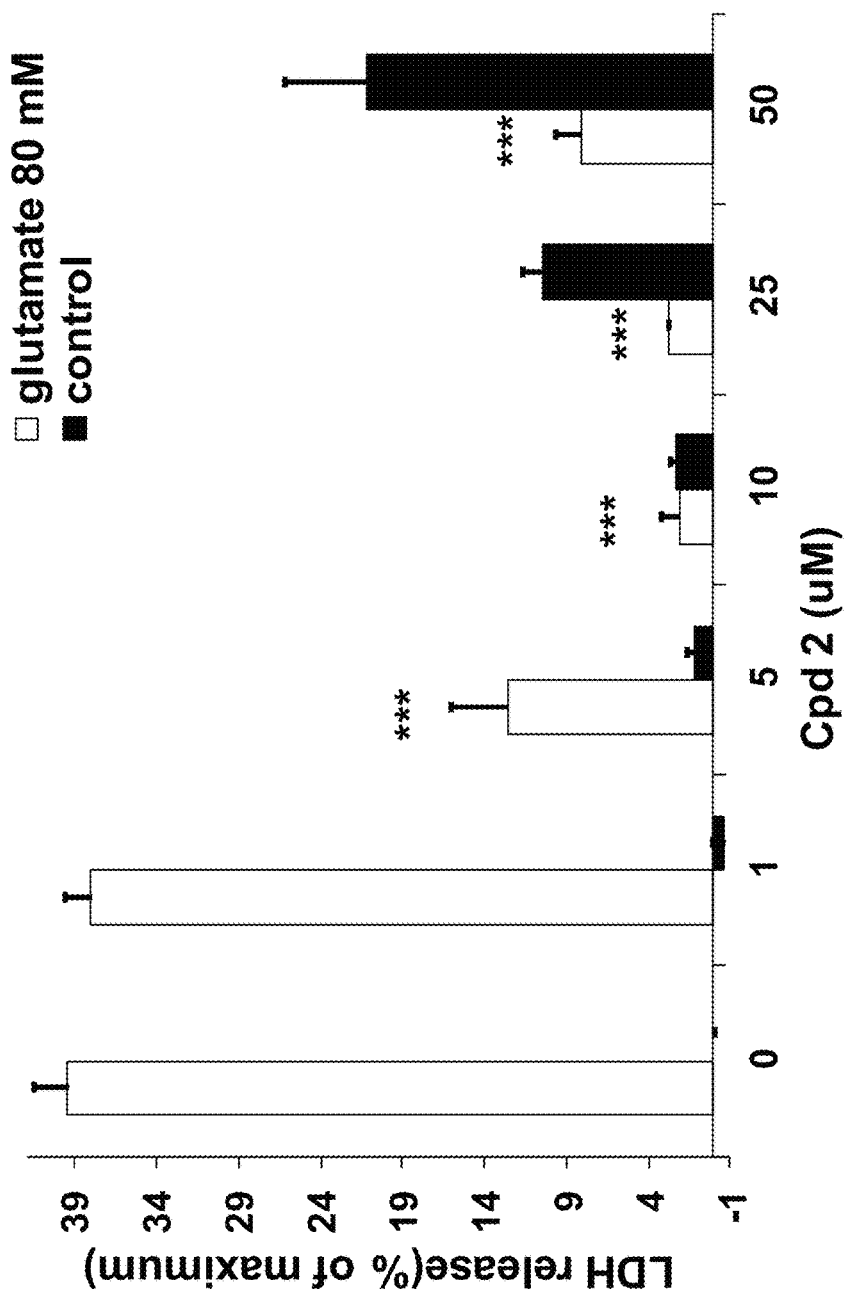
FIG. 2: shows protective properties of compound 2 (characterized by a rotatable phenyl ring halogenated with Cl and F) in vitro. n=4, results are depicted as average±SEM. ***: One way ANOVA gave $p<0.0001$; Bonferroni Multiple Comparisons Test gave $p<0.001$ for glutamate vs. glutamate+compound 2 (5-50 µM). The white columns present exposure to glutamate without (0) or with Cpd 2 (1, 5, 10, 25, 50 µM). The black columns present treatment with only Cpd 2.

Next, the fluorescent dye 10-N-Nonyl-Acridine Orange (NAO) was applied to measure reactive oxygen species (ROS) generation at mitochondrial levels. This ROS generation is typically induced by glutamate and normally under the control of the TSPO. FIG. 1C shows that Compound 1 prevents ROS generation at mitochondrial levels otherwise induced by glutamate (Results are depicted as AVG±SD). FIG. 2 shows that Compound 2, which has moderate affinity for TSPO (Table 1), has strong protective properties in vitro against glutamate induced cell death in U118MG cells. Results are depicted as AVG±SEM. ***: One way ANOVA gave $p<0.0001$; Bonferroni Multiple Comparisons Test gave $p<0.001$ for glutamate vs. glutamate+compound 2 (5-50 μM). In FIG. 2, the white columns present exposure to glutamate without (0) or with Cpd 2 (1, 5, 10, 25, 50 μM). The black columns present treatment with only Cpd 2.

FIG. 3 shows that Compound 3, which has affinity for TSPO (Table 1), has good protective properties in vitro against glutamate induced cell death in U118MG cells. Results are depicted as AVG±SEM. ***: One way ANOVA gave $p<0.0001$; Bonferroni Multiple Comparisons Test gave $p<0.001$ for glutamate vs. glutamate+compound 3 (5-50 μM). In FIG. 3, the white columns present exposure to glutamate without (0) or with Cpd 3 (1, 5, 10, 25, 50 μM). The black columns present treatment with only Cpd 3.

FIG. 4 shows that Compound 4, which has good affinity for the TSPO (Table 1), protects neuronal cells from the SH SY 6Y cell line against lethal effect of glutamate in vitro. Results are depicted as AVG±SEM. n=6, **=$p<0.01$ One way ANOVA with Mann-Whitney as posthoc. Control: no glutamate. Control: no glutamate exposure and no Cpd 4 treatment. Cpd 4: only Cpd 4 treatment. Glut: only glutamate exposure. Cpd 4+glut: glutamate exposure together with glutamate treatment.

Based on these results (FIGS. 1-4), systemic modifications to Compound 1 were studied and applied to compound 1 to determine components that are preferable for beneficial effects (FIGS. 7-9).

FIG. 7. Compound A differs from Compound 1 in that it has two methyl side chains (i.e., symmetric amide) instead of the one methyl and the one ethyl in Compound 1 (i.e., asymmetric amide).

Compound 5 differs from Compound 1 in that it has two methyl side chains instead of one methyl and one ethyl, and a Cl substituted to the 2 position of the third (rotatable) phenyl.

Compound 6 differs from Compound 1 in that it has a Cl substituted to the 2 position of the third (rotatable) phenyl.

Compound 7 differs from Compound 1 in that it has two ethyl side chains instead of one methyl and one ethyl.

Compound 8 differs from Compound 1 in that it has two ethyl side chains instead of one methyl and one ethyl, and a Cl substituted to the 2 position of the third (rotatable) phenyl.

It was found that Compounds A and 5 ($R^1$ and $R^2$ are methyl) both have a Ki of ±600 nM.

It was further found that Compounds 1 and 6 ($R^1$ is methyl and $R^2$ is ethyl) both have a Ki of ±60 nM.

It was further found that Compounds 7 and 8 both $R^1$ and $R^2$ are ethyl) have a Ki of ±2.5 nM.

FIGS. 8A-F show activities of Reference Compound A (FIG. 8A) and Compounds 5, 1, 6, 7 and 8 of the invention (FIG. 8B-F, respectively).

The experimental setup is explained using FIG. 8B as an example:
1. Control: Cell death levels are taken as 0%
2. Glu: Cell death levels induced by glutamate are over 50%
3. Cpd 5: By itself, Cpd 5 does not induce cell death levels over 5%.
4. Glu+Cpd 5: When Cpd 5 is given as a treatment to counteract cell death induced by glutamate, increasing concentrations of Cpd 5 reduce cell death levels from over 50% to less than 5%.

The results presented as (AVG±SD) show that addition of halogen to the rotatable phenyl improves protection (compare FIG. 8A to 8B; FIG. 8C to 8D; and FIGS. 8E to 8F). Addition of a halogen to the rotatable phenyl also reduces lethality of the compounds at high concentrations in otherwise untreated cells (compare FIG. 8A to 8B; FIG. 8C to 8D). Furthermore, introducing asymmetry to the alkyl side chain enhances protection against cell death (compare, e.g., FIGS. 8A to 8C; and 8B to 8D). "Moderate" affinity provided by alkyl modifications (Ki~60 nM) provides optimal protection. #$p<0.05$ vs. vehicle control (control), ###$p<0.001$ vs. vehicle control (control), * $p<0.05$ vs. glutamate exposed (glu), *** $p<0.001$ vs. glutamate exposed cells (glut).

Compounds 1, 5 and 6 appear to be superior over Compounds A (U.S. Pat. No. 8,541,428), 7, and 8 in that they protect better and more consistently at the concentrations of 10, 25, 50, and 100 μM against glutamate induced cell death. In addition, compound 6 appears to be superior over compound 1 in that in general it protects better at concentrations of 10, 25, 50, and 100 μM against glutamate induced cell death. Compound 5 appears to be superior over the rest of the compounds in the current experiment.

Overall, the desired effects are of the compounds are: i) minor lethal effects of the compounds themselves, and ii) consistent reductions of cell death levels otherwise induced by glutamate.

Based on the foregoing, and without wishing to be bound by a particular theory or mechanism of action, it appears that elongation of the alkyl chains $R^1$, $R^2$, improves TSPO binding.

FIG. 9. Details of potential adverse effects of 100 μM of compounds A, 1, 5, 6, 7 and 8 were studied further. The slight lethal effects, if present, of the compounds of the invention could be further reduced by halogenations (using Cl as a non-limiting example) of the third rotatable phenyl.

Example 4: Pharmacokinetic Properties

1) Compound 1 is absorbed from the site of the i.p. administration, good half-life in the mouse of 3.5 hrs.
2) It is quite quickly distributed to the brain (concentration time profiles follow each other)
3) Uptake ratio to the brain is 0.2.
4) The vehicles used, DMSO/Sesame oil (1:9) or DMSO alone, injected subcutaneously or intraperitoneally, show no adverse effects in mice and rats. With chronic subcutaneous injections, Sesame oil could induce hair loss around the ears of the mice in question.

Therefore, the vehicle of choice is pure DMSO, since it has no such or other adverse effect, when injected in small quantities of 10-20 μl in mice and around 200 μl in rats, injected daily over periods of several weeks to several months.

Example 5—Superior Lifespan Extending Effects of Compound 1 in R6-2 Mice, a Transgenic Mouse Model for Huntington Disease R6-2 is a transgenic mouse model for Huntington Disease. Huntington Disease in humans is a hereditary neurodegenerative disease affecting motor performance and finally leading to death of the patients having the disease. R6-2 mice (~120 CAG repeats B6CBA-Tg(HDexon1)62 Gpb/3J) mice were used for the experiments described below. For this purpose, mice obtained from the Jackson Laboratory (ME) were bred. In particular: males genotype: Hemizygous for Tg(HDexon1)62 Gpb, and females from the wildtype background strain B6CBAF1/J were bred according to the protocol of Jackson Laboratory. The male heterozygote offspring (R6-2 mice) were used for determining life span and motor activity, with and without drug treatment. Drug treatment consisted of daily (5 continuous days a week) subcutaneous injections of mice with 20 μl of: saline (sham control), vehicle DMSO (vehicle control), classic TSPO ligand PK 11195 (15 mg/kg), prior art Compound A (15 mg/kg), Compound 1 (15 mg/kg), and compound 1 (7.5 mg/kg). Drug treatment started on week 5 after birth. Quantities were used according to previous studies regarding TSPO ligands.

Apart from the behavioral experiments, mice were observed daily, and the day of death was noted. Behavioral experiments included distance covered in an open field apparatus, and tremor measurements.

Open Field

The open field is made of a black lusterless Perspex box ($50_L \times 50_W \times 40_H$ cm) placed in a dimly lit room (50 lx), its floor made from white Perspex to achieve visual contrast with black mice. Mice are placed in the corner of the open field (facing the wall) and then given 5 min of free exploration. The behavior is videotaped by a CCTV Panasonic camera and post-recording analysis with Ethovision XT 7.0 software (Noldus, The Netherlands), according to: Lemoine et al. *Pharmacology Biochemistry and Behavior.* 1990; 36:85-88.

Tremor Apparatus

To assay incidence of tremor in R6-2 mice of the experiments for this invention, the StartleMonitor of Kinder Scientific (Poway, Calif.), with specific software to assay and present force pressure changes in newtons, was used.

Figure 5A:
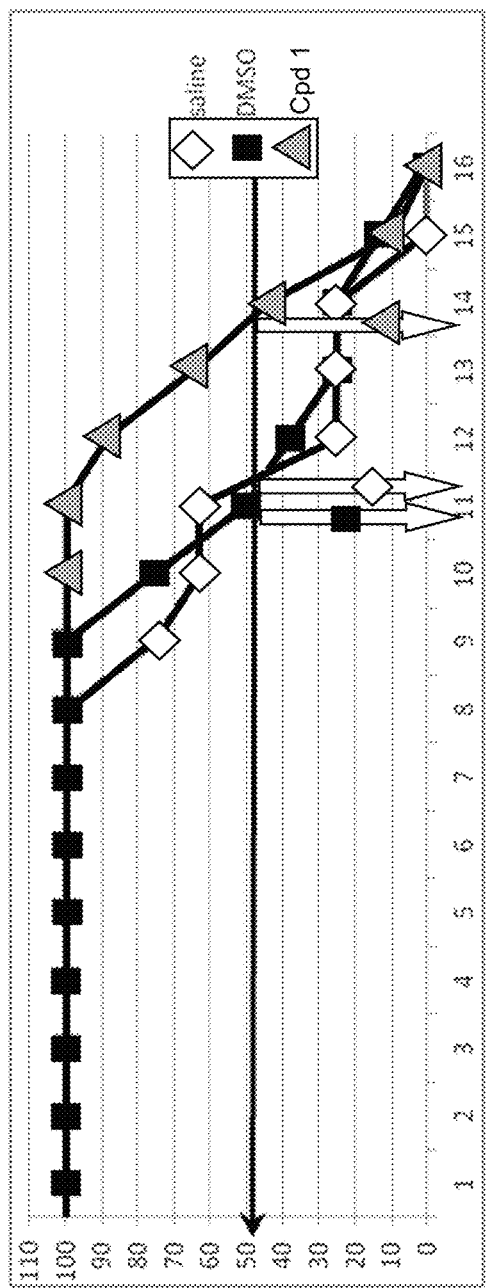
FIG. 5: Effects of Compound 1 in an animal model. A) Compound 1 extends the life span of R6-2 mice, a transgenic model of Huntington Disease compared to vehicle treated (DMSO) and sham treated (saline) R6-2 mice. R6-2 mice present a transgenic mouse model for the neurodegenerative disease of Huntington. No difference is found between DMSO treated and saline treated R6-2 mice. B) The comparative prior art Compound A has no effect in this Huntington disease model, as compared to DMSO and saline treated R6-2 mice. Also, the classical TSPO ligand PK 11195 has no effect at all in this Huntington disease model (data not shown).

FIG. 5A shows that Compound 1 increases average lifespan in R6-2 mice. Compared to the controls presented by saline sham treated and vehicle DMSO treated mice of the transgenic R6-2, Compound 1 increases the average lifespan compared to sham and vehicle treated mice of the transgenic R6-2 model for Huntington Disease. In this paradigm, the effects of saline and DMSO are indistinguishable from each other. Regarding the beneficial effect of Compound 1, onset of death events is later and the average lifespan is longer for R6-2 mice treated with Compound 1, which is considerably and significantly favorable as compared with control R6-2 mice. The y-axis presents the percentage of surviving animals per week. The x-axis presents the number of weeks from birth. For all the experimental groups, the 50% survival cut-off is marked with an extended horizontal black arrow. For each experimental group, the week where this 50% survival cut off is reached is marked with a vertical arrow shown the same symbols as the associated life span curves (square, triangle, and diamond, see FIG. 5A, figure legend). Regarding average survival per week from week 9: Compound 1 vs. saline p<0.01; Compound 1 vs. DMSO p<0.05; DMSO vs. saline n.s. (n=8 to 9).

Figure 5B:
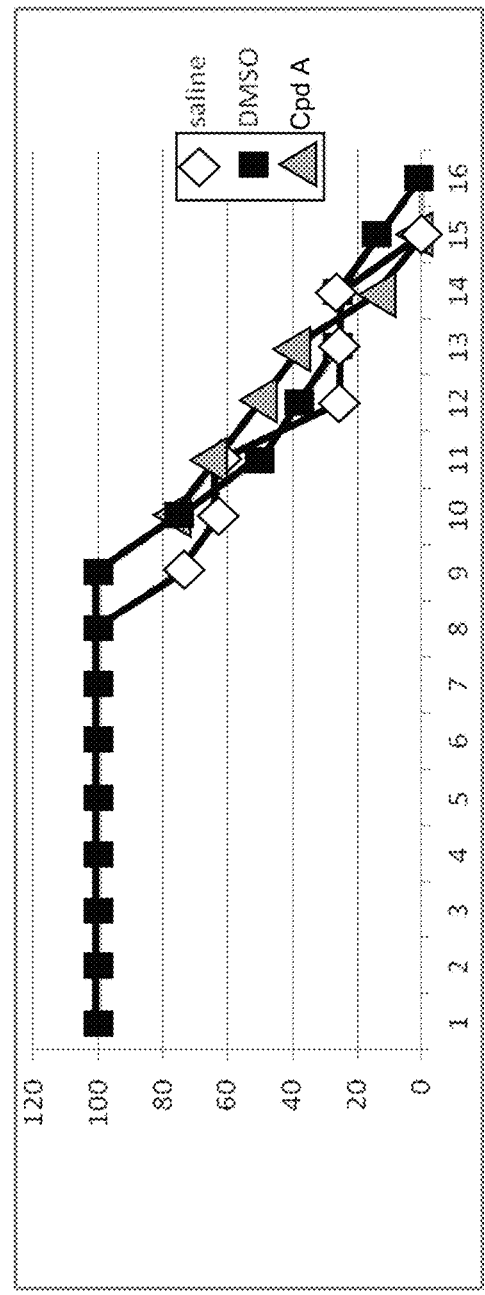

FIG. 5B shows that in comparison to Compound 1, prior art Compound A is unexpectedly significantly less efficacious at extending the lifespan of R6-2 mice. In fact, R6-2 mice treated with Compound A are indistinguishable from vehicle treated mice as well as saline treated mice. Similarly, R6-2 mice treated with the classical TSPO ligand PK 11195 are indistinguishable from vehicle as well as saline treated mice, also regarding their lifespan (data not shown).

Figure 6:
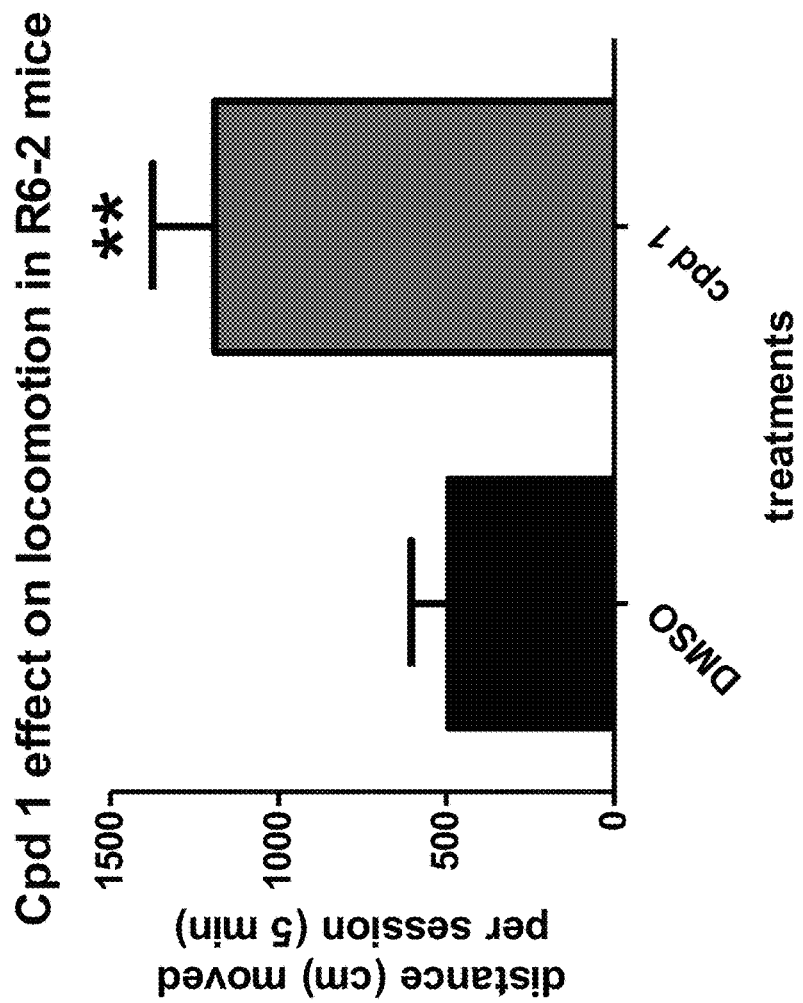
FIG. 6: Compound 1 enhances locomotor activity of R6-2 mice compared to vehicle treated (DMSO shown in the figure) R6-2 mice and sham treated (saline not shown in the figure) R6-2 mice. The comparative prior art Compound A has no effect at all in this Huntington disease model (data not shown). Also the classical TSPO ligand PK 11195 has no effect at all in this Huntington disease model (data not shown). ** $p<0.01$ Cpd 1 treated R6-2 mice vs. vehicle treated R6-2 mice (DMSO).

Example 6—Superior Locomotor Improving Effect of Compound 1 in R6-2 Mice, a Transgenic Mouse Model for Huntington Disease FIG. 6. Compound 1 increases locomotion of R6-2 mice. As measured in an open field compared to untreated and vehicle treated mice of the transgenic R6-2 model for the Huntington disease, Compound 1 significantly enhances locomotor activity of R6-2 mice compared to their vehicle controls. Compound 1 also enhanced locomotor activity compared to sham (saline) control. In particular, from week 9, when the first mice death occurred, until week 16, when all mice were dead, average distance covered in an open field, per session, per experimental group, per week was measured in cm. No adverse effects due to Compound 1 application are observed. Compound 1 vs. DMSO p<0.01; Compound 1 vs. saline trend (not shown). In comparison, prior art Compound A and PK 11195 did not show any locomotor improving effects (data not shown)

Example 7

Figure 10:
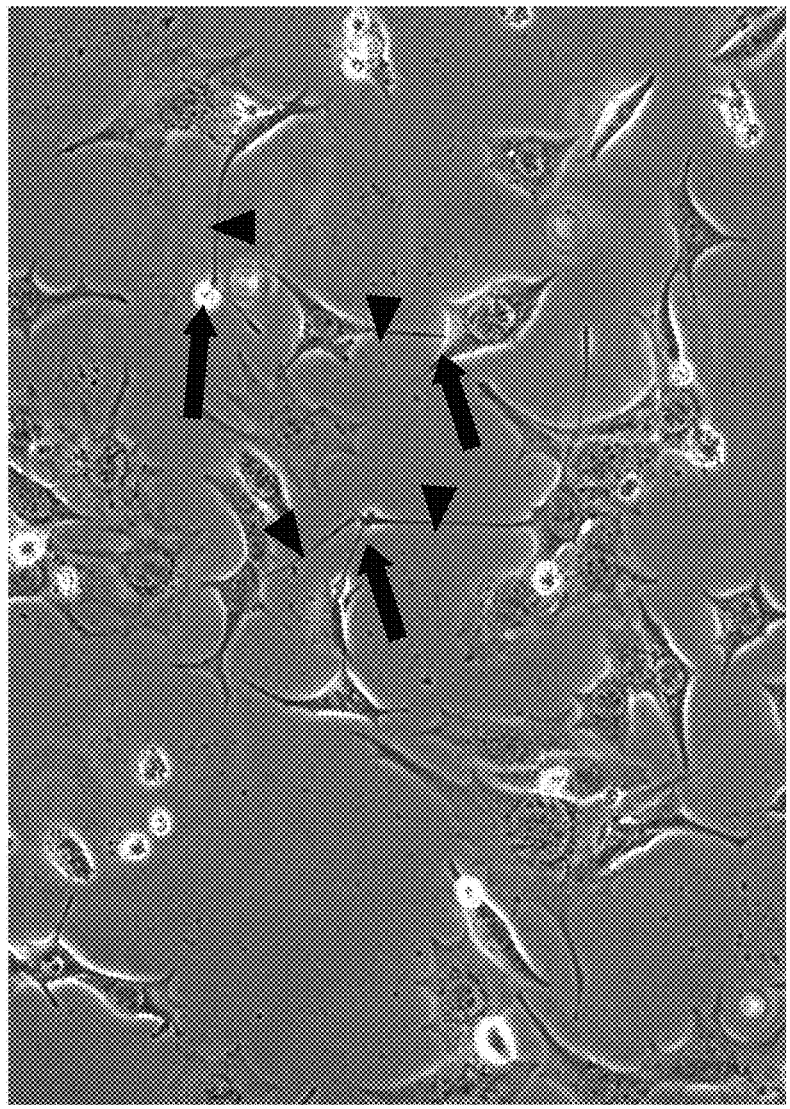
FIG. 10: In cell culture, given together with glutamate, Cpd 1 can induce differentiation of PC12 cells toward neuronal type cell as characterized by outgrowth of neurites resembling axons. Other compounds of the present invention have the same effects (while classical TSPO ligands reportedly are not effective regarding this kind of differentiation). The triangles point at neurites resembling axons as induced by application of Cpd 1. The arrows point at potential contact sites.

Cpd 1 is able to transform PC-12 cells in cell culture to neuron like cells displaying extended neurites that define such neuronal differentiation (FIG. 10). Briefly, PC-12 cells were exposed to Cpd 1, in combination with glutamate, basically as described for the cell cultures of Example 1, and remained under that condition for 5 days. This resulted in neuron like cells with axon like protrusions (FIG. 10).

Example 8: Superior Lifespan Extending Effects of Compounds 5 and 6 in R6-2 Mice, a Transgenic Mouse Model for Huntington Disease R6-2 mice were used as previously described in Example 5. In one experiment, treatment consisted of daily (5 continuous days per week) subcutaneous injections of mice with 20 µl of vehicle DMSO (control, n=10) and Compound 6 (7.5 mg/kg, n=12). In a separate experiment, compound 5 (7.5 mg/kg, n=5) was tested, compared to DMSO control (n=5).

Figure 12:
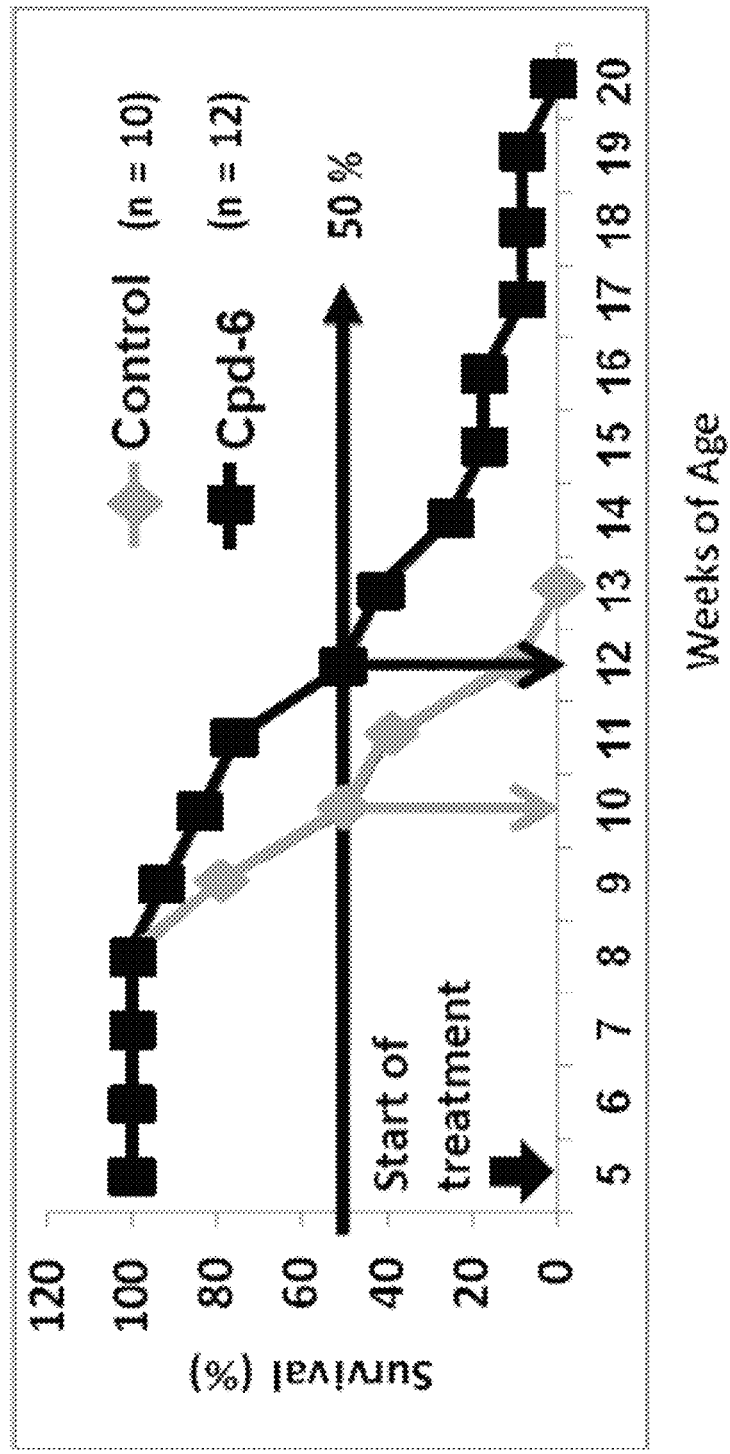
FIG. 12: Compound 6 (a halogenated derivative of compound 1) extends the life span of R6-2 mice compared to vehicle treated (DMSO) R6-2 mice. The vertical lines represent the median lifespan in each treatment group.
Figure 13:
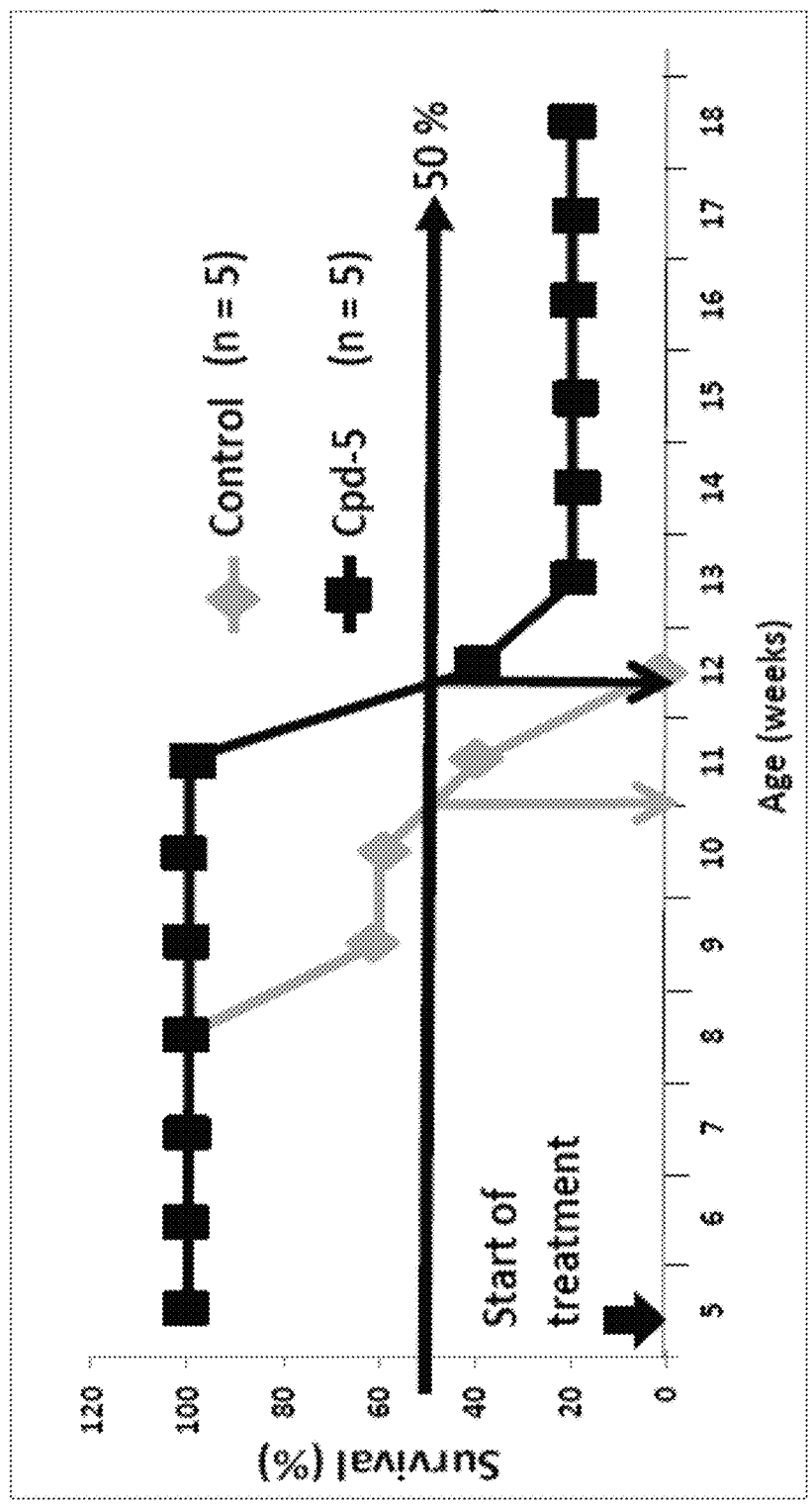
FIG. 13: Compound 5 (a halogenated derivative of compound A) extends the life span of R6-2 mice compared to vehicle treated (DMSO) R6-2 mice. The vertical lines represent the median lifespan in each treatment group.

FIGS. 12 and 13 show that Compounds 6 and 5 (respectively) increase the average lifespan of transgenic R6-2 mice, compared to the vehicle (DMSO) treated mice.

As shown in FIG. 12, 50% of vehicle (DMSO) treated mice died before their 10th week, while 50% of the R6-2 transgenic mice treated with compound 6 were still alive until the 12th week. The y-axis presents the percentage of surviving animals per week. The x-axis presents the number of weeks from birth. The 50% survival cut off is marked with a horizontal arrow. For each experimental group, the week where the 50% survival cut off is reached is marked with vertical arrow. Applying ANOVA and Wilcoxon matched-pairs signed rank test regarding the number of surviving animals indicates a significant difference between the R6-2 mice treated with compound 6 and the DMSO (vehicle) injected R6-2 mice: p<0.01. Applying Mann-Whitney to each week of treatment shows that at the week of 50% survival of the R6-2 mice treated with compound 6 (week 12 of age) and the week thereafter, the differences between the treated R6-2 mice and the vehicle injected R6-2 mice were significant p<0.05 for each of these two weeks. To determine whether the death rate of the vehicle injected R6-2 mice is steeper than the death rate of R6-2 mice treated with compound 6, a linear regression model was applied. Looking over the whole survival periods of both groups, and also over the restricted period from the week of diagnosis (week 8, after which the first animals have died) until all of the vehicle treated R6-2 mice have died (week 13), in both instances a significant difference between slopes is seen, p<0.01 (F=12.5 and 20.8 respectively).

As shown in FIG. 13, >50% of vehicle (DMSO) treated mice died before their 11th week, at which point 100% of the mice treated with compound 5 were still alive. Furthermore, at 12 weeks, all of the vehicle (DMSO)-treated mice were dead while 50% of the mice treated were compound 5 were still alive, and 20% of the treated mice continued to live up to 18 weeks. The y-axis presents the percentage of surviving animals per week. The x-axis presents the number of weeks from birth. The 50% survival cut off is marked with a horizontal arrow. For each experimental group, the week where the 50% survival cut off is reached is marked with vertical arrow.

Example 9: Synthesis Protocols

All reactions involving air- and moisture-sensitive compounds were carried out under argon atmosphere, using flamed flask and dry, oxygen-free solvents. 1,2-Dimethoxyethane were distilled under argon from $CaH_2$. Flash chromatography (FC) was performed using silica gel 60 (230-400 mesh). Thin layer chromatography was performed using precoated plates (silica gel 60, 0.25 mm). All NMR spectra were recorded at room temperature with Bruker-Avance-300 instruments at operating frequencies 300 MHz ($^1$H) or 75 MHz ($^{13}$C) respectively. Chemical shifts are referenced to the residual proton or carbon resonance of the deuterated solvent (chloroform δ=7.24 for $^1$H NMR or δ=77.00 for proton decoupled $^{13}$C NMR, and (J) in (Hz).

General Procedure (Scheme 1)

The compounds of the invention may be prepared by the process described in general Scheme 1 hereinabove, and in Scheme 2 below. Briefly, to a suspension of (6.75 mmol) potassium hydride under argon in 30 ml of 1,2-dimethoxyethane (DME) is added the alcohol (4.5 mmol) in one portion. The reaction mixture is stirred for 30 minutes at room temperature and carbamoyl chloride (7 mmol) is added to the reaction mixture. Reaction mixture is brought to reflux for 2-5 hrs till completion of reaction (TLC monitored). The reaction is quenched with 30 ml of water carefully, followed by extraction with dichloromethane (or ethyl acetate). Combined organic phases are dried over $MgSO_4$ and the solvents are evaporated under reduced pressure. The resulting crude product is purified by silica gel chromatography hexane/EtOAc as eluent (2/1 for compounds 1, 2, 3, and 4, and 85/15 for compounds 5, 6, 7, and 8). The pure compound after purification was crystallized with DCM/ethylacetate/n-pentane to get the solid form.

The process is exemplified hereinbelow for Compound 1. However, other compounds of the invention may be prepared by a similar method as generally described in Schemes 1 and 2.

2-phenylquinazolin-4-yl ethyl(methyl)carbamate (Compound 1)

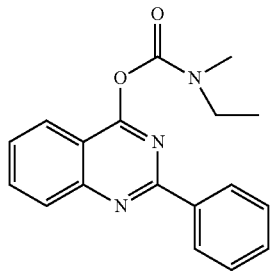

1

The title product was obtained as white solid in 65% yield. $^1$H NMR (300 MHz, CDCl$_3$) δ 1.32 (t, J=7 Hz, 1.5H, rotamer 1), 1.33 (t, J=7 Hz, 1.5H, rotamer 2), 3.12 (s, 1.5H, rotamer 1), 3.13 (s, 1.5H, rotamer 2), 3.50-3.59 (m, 2H), 7.45-7.50 (m, 3H), 7.54-7.59 (m, 1H), 7.85-7.90 (m, 1H), 8.04-8.09 (m, 2H), 8.51-8.55 (m, 2H). $^{13}$C NMR (75 MHz, CDCl$_3$) δ 12.23 (rotamer 1), 13.40 (rotamer 2), 34.40 (rotamer 1), 34.46 (rotamer 2), 44.55 (rotamer 1), 44.84 (rotamer 2), 115.81 (rotamer 1), 116.19 (rotamer 2), 123.25 (rotamer 1), 123.29 (rotamer 2), 127.11 (rotamer 1), 127.15 (rotamer 2), 128.28 (rotamer 1), 12.32 (rotamer 2), 128.36, 128.56 (rotamer 1), 128.59 (rotamer 2), 130.63, 134.21, 137.28, 153.12 (rotamer 1), 153.20 (rotamer 2), 160.26 (rotamer 1), 160.34 (rotamer 2), 164.05 (rotamer 1), 164.14 (rotamer 2), 179.10. HRMS (ESI): Mass calcd for C$_{18}$H$_{18}$N$_3$O$_2$ [M+H]$^+$: 308.1399; found: 308.1350. Compound 1 can be recrystallized from Hexane/EtOAc (1:3).

Figure 11:
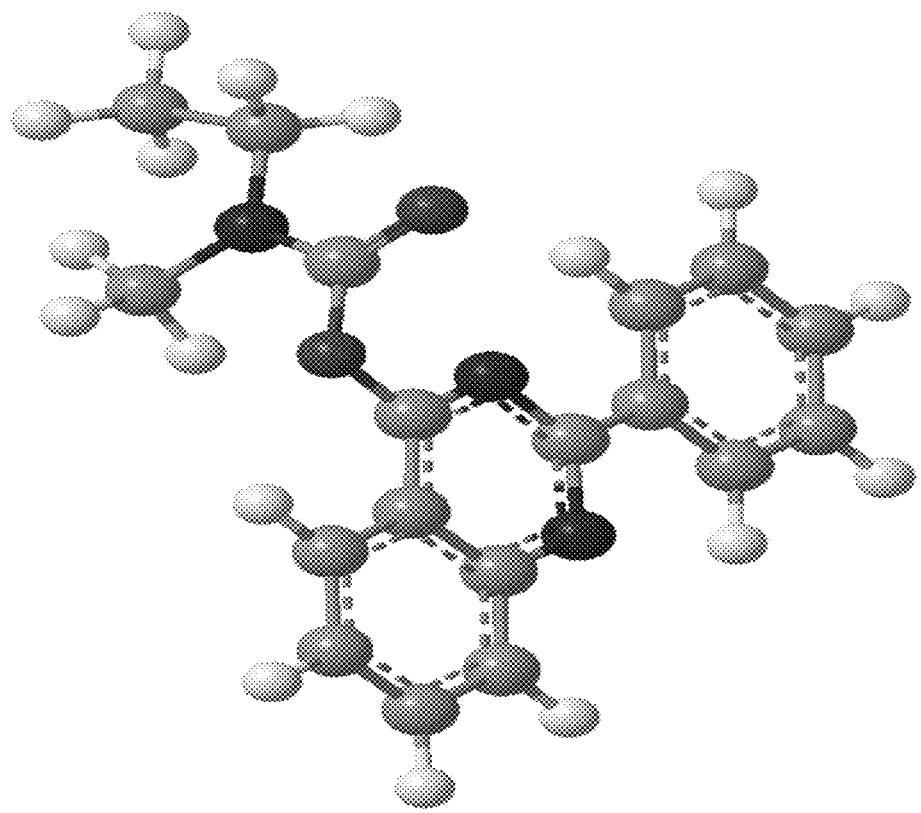
FIG. 11: X-ray determined ball and stick structure of compound 1.

The X-ray determined structure of Compound 1 is depicted in a ball and stick representation in FIG. 11.

2-(3-chloro-4-fluorophenyl)quinazolin-4-yl diethylcarbamate (Compound 2)

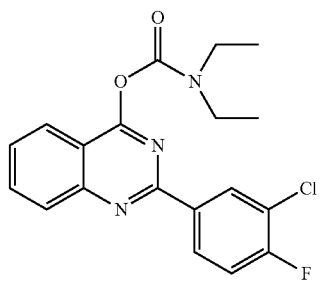

2

The title product was obtained as white solid in 57% yield. $^1$H NMR (300 MHz, CDCl$_3$) δ 1.24-1.43 (m, 6H), 3.41-3.60 (m, 4H), 7.22 (t, J=8.8 Hz, 1H), 7.59 (dd, J=8.2 & 7.0 Hz, 1H), 7.89 (ddd, J=8.6, 6.9 & 1.5 Hz, 1H), 8.05 (dd, J=9.9 & 8.4 Hz, 2H), 8.43 (ddd, J=8.7, 4.9 & 2.1 Hz, 1H) and 8.61 (dd, J=7.4 & 2.2 Hz, 1H). HRMS (ESI): Mass calcd for C$_{19}$H$_{17}$ClFN$_3$O$_2$ [M+H]$^+$: 373.0993; found: 374.1031.

2-(2,6-dichlorophenyl)quinazolin-4-yl diethylcarbamate (Compound 3)

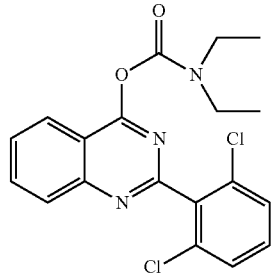

3

The title product was obtained as white solid in 63% yield. $^1$H NMR (300 MHz, CDCl$_3$) δ 1.23 (t, J=7.2 Hz, 3H), 1.30 (t, J=7.2 Hz, 3H), 3.38-3.54 (m, 4H), 7.25-7.42 (m, 3H), 7.70 (dd, J=8.3 & 7.0 Hz, 1H), 7.95 (ddd, J=8.6, 6.9 & 1.5 Hz, 1H) and 8.13 (dd, J=9.4 & 8.4 Hz, 2H). HRMS (ESI): Mass calcd for C$_{19}$H$_{17}$Cl$_2$N$_3$O$_2$ [M+H]$^+$: 390.0698; found: 390.0769.

2-(4-bromophenyl)quinazolin-4-yl diethylcarbamate (Compound 4)

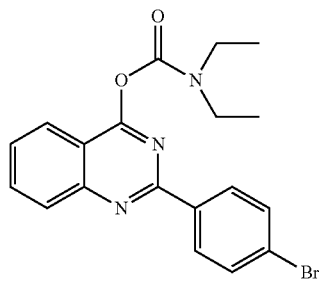

4

The title product was obtained as white solid in 60% yield. $^1$H NMR (300 MHz, CDCl$_3$) $^{TM}$(ppm): 1.13-1.26 (m, 6H), 3.34-3.46 (m, 4H), 7.46-7.51 (m, 2H), 7.53 (d, J=6.5 Hz, 2H), 7.75 (t, J=5.2 Hz, 1H), 7.92 (t, 5.2 Hz, 1H) and 8.37 (d, J=6.5 Hz, 2H). $^{13}$C NMR (75 MHz, CDCl$_3$) $^{TM}$(ppm): 12.7, 14.0, 42.2, 42.3, 115.7, 123.0, 125.1, 127.9, 129.8, 131.2, 134.0, 135.9, 152.7, 159.0 and 163.9. MS: m/z calcd for C$_{19}$H$_{18}$N$_3$O$_2$Br: [M+H]$^+$ 399.06; found: 399.9.

General Reaction for Synthesis of Compounds 5-8

Scheme 2

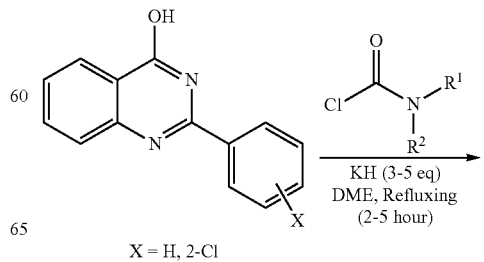

X = H, 2-Cl

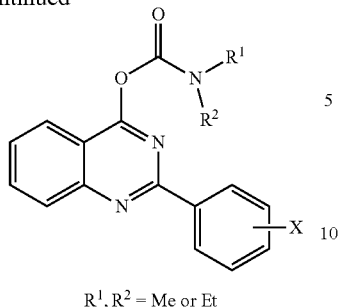

R¹, R² = Me or Et 2-(2-chlorophenyl)quinazolin-4-yl dimethylcarbamate (Compound 5)

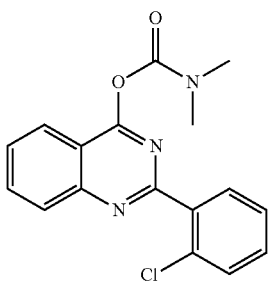

The title product was obtained as white solid in 47% of Yield. ¹H NMR (400 MHz, CDCl₃) δ 3.10 (s, 3H), 3.16 (s, 3H), 7.31-7.42 (m, 2H), 7.44-7.51 (m, 2H), 7.65 (dd, J=8.6 & 7.2 Hz, 1H), 7.80-7.87 (m, 1H), 7.92 (t, J=7.8 Hz, 1H), 8.05-8.21 (m, 2H). ¹³C NMR (100 MHz, CDCl₃) δ 37.34, 116.20, 123.61, 127.00, 130.60, 130.77, 132.26, 133.26, 134.78, 137.73, 152.11, 153.04, 161.17 and 164.11. HRMS (ESI): Mass calcd for $C_{17}H_{14}ClN_3O_2$ [M+H]⁺: 327.0775; found: 327.0000.

2-(2-chlorophenyl)quinazolin-4-yl ethyl(methyl)carbamate (Compound 6)

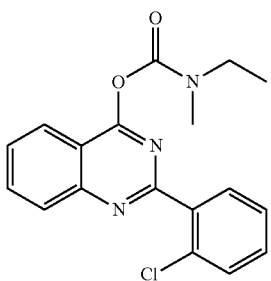

The title product was obtained as white solid in 65% of Yield. ¹H NMR (400 MHz, CDCl₃) δ 1.17-1.32 (m, 3H), 3.04 and 3.08 (2s, 3H), 3.38-3.58 (m, 2H), 7.33 (dd, J=7.0 & 3.2 Hz, 2H), 7.40-7.50 (m, 1H), 7.61 (dd, J=8.6 & 7.4 Hz, 1H), 7.78-7.84 (m, 1H), 7.88 (dd, J=9.4 & 7.2 Hz, 2H) and 8.08 (dd, J=9.5 & 7.2 Hz, 2H). ¹³C NMR (100 MHz, CDCl₃) δ 12.43 & 13.65, 34.64 & 34.74, 44.82 & 45.12, 116.07 & 116.36, 123.52 & 123.57, 126.92, 128.13 & 128.19, 128.60, 130.52, 130.71, 132.23, 133.23, 134.68, 137.70 & 137.72, 151.71 & 151.92, 152.95 & 152.99, 161.09 & 161.15, 164.11 & 164.19. HRMS (ESI): Mass calcd for $C_{18}H_{16}ClN_3O_2$ [M+H]⁺: 341.0931; found: 341.0000.

2-phenylquinazolin-4-yl diethylcarbamate (Compound 7)

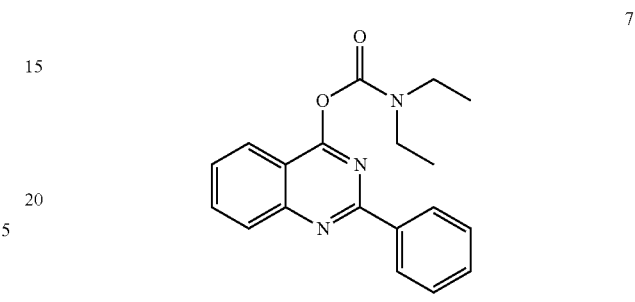

The title product was obtained as white solid in 60% of Yield. ¹H NMR (400 MHz, CDCl₃) δ 1.19-1.42 (m, 6H), 3.32-3.68 (m, 4H), 7.36-7.63 (m, 4H), 7.85 (t, J=6.7 Hz, 1H), 8.05 (d, J=8.3 Hz, 2H) and 8.51 (dd, J=6.6 & 3.0 Hz, 2H). ¹³C NMR (100 MHz, CDCl₃) δ 13.41 & 14.65, 42.90 & 43.00, 116.37, 123.61, 127.42, 128.61, 128.67, 128.91, 130.94, 134.49, 137.63, 151.82, 153.46, 160.63 and 164.57. HRMS (ESI): Mass calcd for $C_{19}H_{19}N_3O_2$ [M+H]⁺: 321.1477; found: 321.0000.

2-(2-chlorophenyl)quinazolin-4-yl diethylcarbamate (Compound 8)

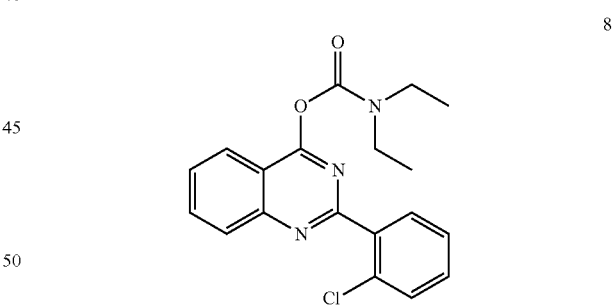

The title product was obtained as white solid in 69% of Yield. ¹H NMR (400 MHz, CDCl₃) δ 1.02-1.55 (m, 6H), 3.23-3.76 (m, 4H), 7.26-7.40 (m, 2H), 7.41-7.53 (m, 1H), 7.57-7.72 (m, 1H), 7.75-7.97 (m, 2H) and 8.01-8.27 (m, 2H). ¹³C NMR (100 MHz, CDCl₃) δ 13.25 & 14.55, 42.85, 116.27, 123.50, 126.86, 128.10, 128.55, 130.47, 130.68, 132.23, 133.21, 137.66, 151.55, 152.92, 161.08 and 164.20. HRMS (ESI): Mass calcd for $C_{19}H_{18}ClN_3O_2$ [M+H]⁺: 355.1088, found: 355.0000.

While certain embodiments of the invention have been illustrated and described, it is clear that the invention is not limited to the embodiments described herein. Numerous modifications, changes, variations, substitutions, and equivalents will be apparent to those skilled in the art without departing from the spirit and scope of the present invention as described by the claims, which follow.

What is claimed is:

1. A compound represented by the structure of Formula (I):

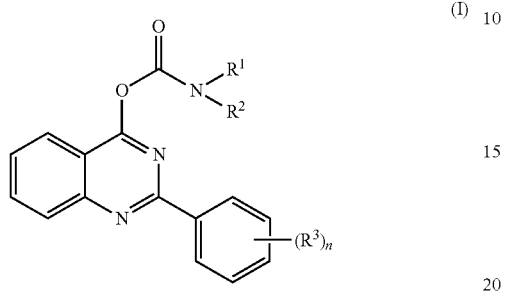

wherein $R^1$ and $R^2$ are each independently a linear or branched $C_1$-$C_{12}$ alkyl;

$R^3$ is a halogen; and n is 1, 2, 3, 4 or 5;

including salts thereof.

2. The compound according to claim 1, wherein $R^1$ and $R^2$ are each independently selected from the group consisting of methyl, ethyl, propyl, isopropyl, n-butyl, sec-butyl, isobutyl and tert-butyl.

3. The compound according to claim 1, wherein $R^1$ is different from $R^2$.

4. The compound according to claim 1, wherein n is 1 or 2.

5. The compound according to claim 1, wherein $R^3$ is Cl, Br or F or a combination thereof.

6. A compound according to claim 1, selected from the group consisting of:

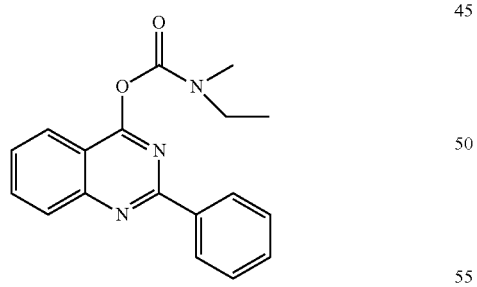

1

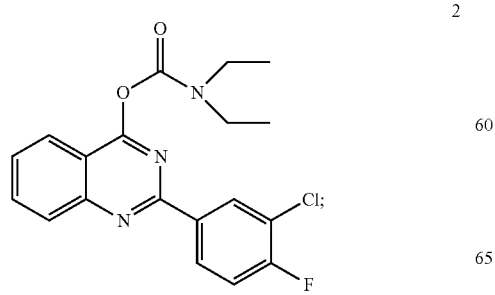

2

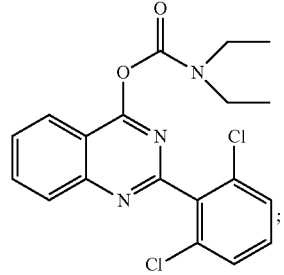

3

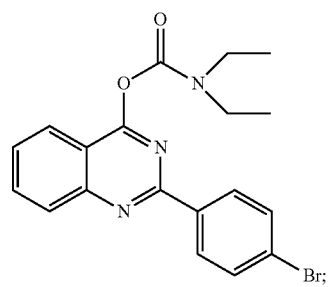

4

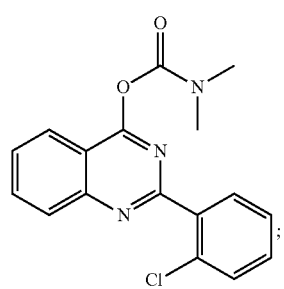

5

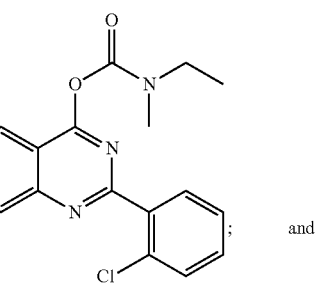

6 and

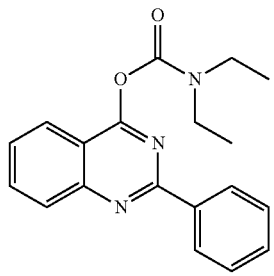

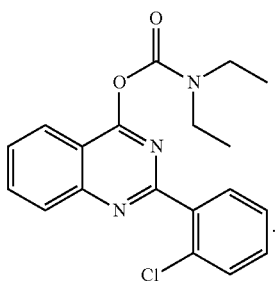

7. The compound according to claim 6, which is represented by the structure of formula 5.

8. The compound according to claim 1, wherein $R^3$ is Cl.

9. A pharmaceutical composition comprising a pharmaceutically acceptable carrier, and as an active ingredient a compound according to claim 1.

10. A method for treating brain damage and/or preventing progression and/or symptoms thereof, wherein the brain damage is due to brain injury resulting from an acute event selected from traumatic brain injury (TBI) and secondary brain damage resulting from TBI, the method comprising the step of administering to a subject in need thereof an effective amount of a compound of claim 1, or a pharmaceutical composition comprising such compound.

11. The method according to claim 10, wherein the brain damage is secondary brain damage resulting from TBI or from agents that are involved in secondary brain damage or neurodegeneration, said agents preferably being selected from glutamate, glutamate receptor ligands other than glutamate, hypoxia mimicking agents, nitric oxide generating agents, apoptosis inducing agents, steroids, ammonium chloride, toxic compounds, and agents which interfere with ATP production; or
wherein the brain damage is due to an acute or a chronic challenge selected from infection, toxins, and excessive drug use of recreational, over the counter, and/or prescription drugs.

12. A method for reducing or treating CNS damage by activating migration, proliferation, adhesion, and/or differentiation, to thereby replenish depleted brain cells in a subject having brain damage due to injury, or who is at risk for developing brain damage due to injury, comprising the step of administering to said subject an effective amount of a compound according to claim 1, or a pharmaceutical composition comprising such compound.

13. A method for preventing programmed cell death in a subject having a neurodegenerative disease, comprising the step of administering to said subject an effective amount of a compound according to claim 1, or a pharmaceutical composition comprising such compound.

14. A method for reducing or treating CNS damage by activating migration, proliferation, adhesion, and/or differentiation, to thereby replenish depleted brain cells in a subject having a neurodegenerative disease, comprising the step of administering to said subject an effective amount of a compound according to claim 1, or a pharmaceutical composition comprising such compound.

15. A method of stimulating or enhancing restorative processes in the CNS, including migration of progenitor cells to damaged brain areas, neurodifferentiation in damaged brain areas, and re-establishment of damaged neuro-circuitry, comprising the step of administering to a subject in need thereof an effective amount of a compound according to claim 1, or a pharmaceutical composition comprising such compound.

16. A method for reducing or treating brain edema, comprising the step of administering to a subject in need thereof an effective amount of a compound according to claim 1, or a pharmaceutical composition comprising such compound.

17. A method for repairing lesions and/or stimulating repair of the spinal cord by inducing axon growth across damaged areas and into their target area, comprising the step of administering to a subject in need thereof an effective amount of a compound according to claim 1, or a pharmaceutical composition comprising such compound.

* * * * *